(12) United States Patent
Devani

(10) Patent No.: US 12,376,773 B2
(45) Date of Patent: Aug. 5, 2025

(54) SYSTEMS AND METHODS FOR OPTICAL EVALUATION OF PUPILLARY PSYCHOSENSORY RESPONSES

(71) Applicant: BioTrillion, Inc., San Francisco, CA (US)

(72) Inventor: Savan R. Devani, San Francisco, CA (US)

(73) Assignee: BioTrillion, Inc., San Francisco, CA (US)

( * ) Notice: Subject to any disclaimer, the term of this patent is extended or adjusted under 35 U.S.C. 154(b) by 385 days.

(21) Appl. No.: 17/758,695

(22) PCT Filed: Jan. 13, 2021

(86) PCT No.: PCT/US2021/013276
§ 371 (c)(1),
(2) Date: Jul. 12, 2022

(87) PCT Pub. No.: WO2021/146312
PCT Pub. Date: Jul. 22, 2021

(65) Prior Publication Data
US 2023/0052100 A1    Feb. 16, 2023

Related U.S. Application Data

(60) Provisional application No. 62/960,566, filed on Jan. 13, 2020.

(51) Int. Cl.
*A61B 3/11*    (2006.01)
*A61B 3/12*    (2006.01)
(Continued)

(52) U.S. Cl.
CPC .............. *A61B 5/163* (2017.08); *A61B 3/112* (2013.01); *A61B 3/1216* (2013.01); *A61B 3/145* (2013.01);
(Continued)

(58) Field of Classification Search
CPC ..................................................... G06V 40/19
See application file for complete search history.

(56) References Cited

U.S. PATENT DOCUMENTS

| | | | |
|---|---|---|---|
| 2002/0024633 A1 | 2/2002 | Daehoon et al. | |
| 2015/0044649 A1* | 2/2015 | Voss ..................... | G06V 40/176 434/236 |

(Continued)

FOREIGN PATENT DOCUMENTS

| | | | | |
|---|---|---|---|---|
| CN | 111222374 A | * | 6/2020 | |
| EP | 2583619 A1 | * | 4/2013 | ........... A61B 3/0025 |

(Continued)

OTHER PUBLICATIONS

Debie et al. "Multimodal fusion for objective assessment of cognitive workload: A review." IEEE transactions on cybernetics 51.3, 1542-1555 (2019).

(Continued)

*Primary Examiner* — Di Xiao
(74) *Attorney, Agent, or Firm* — Nixon Peabody LLP

(57) ABSTRACT

The present disclosure is directed to systems and methods for measuring and analyzing pupillary psychosensory responses. An electronic device is configured to receive video data with at least two frames. The electronic device then locates one or more eye objects in the video data and determine pupil and iris sizes of the one or more eye objects. The electronic device determines the pupillary psychosensory responses of the one or more eye objects by tracking a ratio of pupil diameter to iris diameter throughout the video. Several metrics for the pupillary psychosensory responses can be determined (e.g., velocity of change of the ratio, peak to peak amplitude of the change in ratio over time, etc.). These metrics can be used as measures of an individual's (Continued)

cognitive ability and mental health in a single session or tracked throughout multiple sessions.

18 Claims, 20 Drawing Sheets

(51) Int. Cl.
*A61B 3/14* (2006.01)
*A61B 5/00* (2006.01)
*A61B 5/16* (2006.01)
*G06T 7/00* (2017.01)
*G06V 40/18* (2022.01)

(52) U.S. Cl.
CPC .......... *A61B 5/4088* (2013.01); *A61B 5/7275* (2013.01); *G06T 7/0016* (2013.01); *G06V 40/193* (2022.01); *G06T 2207/10016* (2013.01); *G06T 2207/20081* (2013.01); *G06T 2207/30041* (2013.01)

(56) References Cited

U.S. PATENT DOCUMENTS

| | | | |
|---|---|---|---|
| 2015/0116665 A1 | 4/2015 | Finkel et al. | |
| 2015/0220768 A1* | 8/2015 | Ronnecke | G06V 40/10 348/78 |
| 2016/0187654 A1* | 6/2016 | Border | G02B 27/0172 359/630 |
| 2017/0367633 A1 | 12/2017 | Samadani | |
| 2018/0365491 A1* | 12/2018 | Delaney | G06Q 50/18 |
| 2019/0191995 A1 | 6/2019 | Giovinazzo et al. | |
| 2020/0155789 A1* | 5/2020 | Jameson | G16H 50/20 |

FOREIGN PATENT DOCUMENTS

| | | | | |
|---|---|---|---|---|
| EP | 3730998 A1 * | 10/2020 | ........ | G01M 11/0228 |
| JP | 2019522514 A * | 6/2016 | | |
| WO | WO-2016160286 A1 * | 10/2016 | ........... | A61B 3/0025 |

OTHER PUBLICATIONS

Karahan et al. "Eye detection by using deep learning." 24th Signal Processing and Communication Application Conference (SIU), IEEE (2016) [English abstract].

Rozado et al. "Combining EEG with pupillometry to improve cognitive workload detection." Computer 48.10, 18-25 (2015).

Wangwiwattana et al. "Pupilnet, measuring task evoked pupillary response using commodity rgb tablet cameras: Comparison to mobile, infrared gaze trackers for inferring cognitive load." Proceedings of the ACM on Interactive, Mobile, Wearable and Ubiquitous Technologies 1.4, 1-26 (2018).

International Search Report and Written Opinion in International Application No. PCT/US2021/13276, mailed Apr. 2, 2021 (7 pages).

* cited by examiner

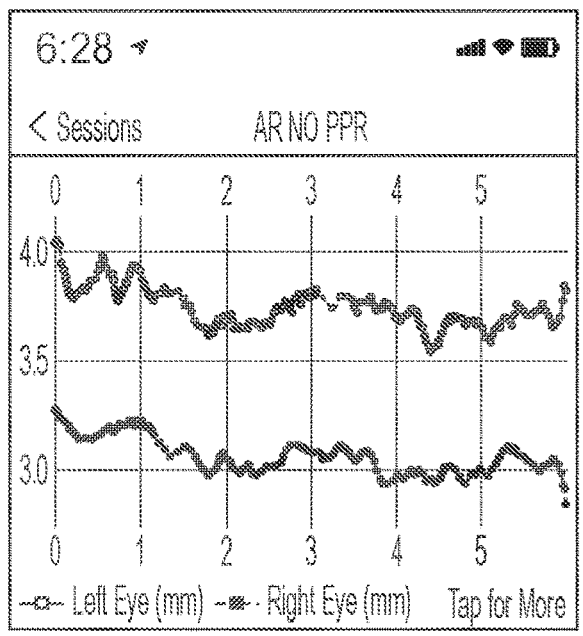
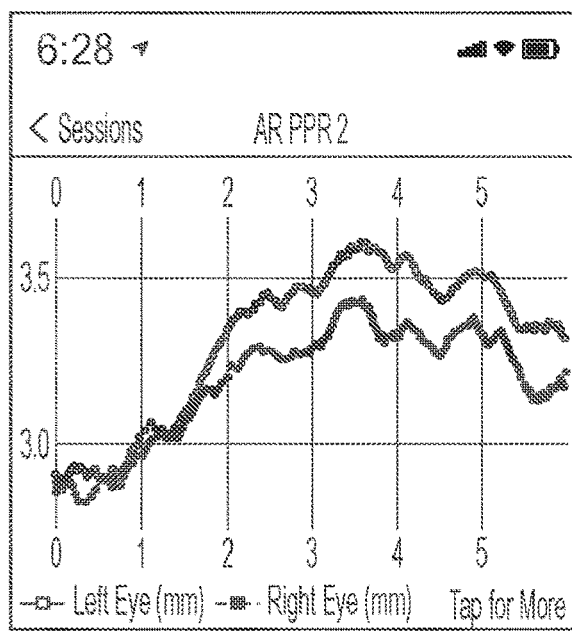

LEFT EYE
Latency                  : 0.0 ms
Maximum Diameter         : 4.053 mm
Minimum Diameter         : 3.610 mm
Average Diameter         : 3.745 mm
Constriction Time        : 1.783 s
Avg Constriction Velocity: 0.248 mm/s
Max Constriction Velocity: 3.155 mm/s
Max Constriction Amplitude: 0.443 mm
Constriction Ratio       : 89.1%

RIGHT EYE
Latency                  : 0.0 ms
Maximum Diameter         : 3.275 mm
Minimum Diameter         : 2.965 mm
Average Diameter         : 3.059 mm
Constriction Time        : 2.333 s
Avg Constriction Velocity: 0.133 mm/s
Max Constriction Velocity: 1.176 mm/s
Max Constriction Amplitude: 0.310 mm
Constriction Ratio       : 90.5%

*Play Debug Movie*

FIG. 5-2A

LEFT EYE
Latency                  : 0.0 ms
Maximum Diameter         : 2.938 mm
Minimum Diameter         : 2.880 mm
Average Diameter         : 3.315 mm
Constriction Time        : 0.317 s
Avg Constriction Velocity: 0.181 mm/s
Max Constriction Velocity: 0.860 mm/s
Max Constriction Amplitude: 0.057 mm
Constriction Ratio       : 98.1%

RIGHT EYE
Latency                  : 0.0 ms
Maximum Diameter         : 2.899 mm
Minimum Diameter         : 2.820 mm
Average Diameter         : 3.187 mm
Constriction Time        : 0.233 s
Avg Constriction Velocity: 0.337 mm/s
Max Constriction Velocity: 0.820 mm/s
Max Constriction Amplitude: 0.079 mm
Constriction Ratio       : 97.3%

*Play Debug Movie*

FIG. 5-2B

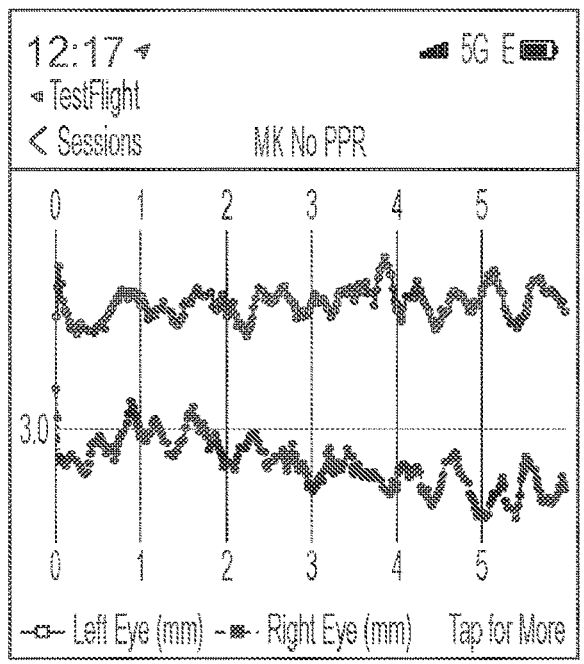
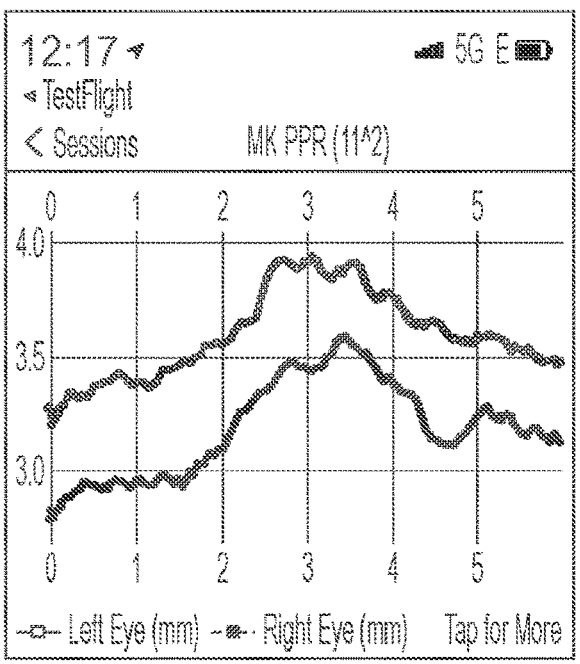

LEFT EYE
Latency                 : 0.0 ms
Maximum Diameter        : 3.234 mm
Minimum Diameter        : 3.135 mm
Average Diameter        : 3.182 mm
Constriction Time       : 2.183 s
Avg Constriction Velocity : 0.045 mm/s
Max Constriction Velocity : 1.362 mm/s
Max Constriction Amplitude : 0.099 mm
Constriction Ratio      : 96.9%

RIGHT EYE
Latency                 : 0.0 ms
Maximum Diameter        : 3.058 mm
Minimum Diameter        : 2.918 mm
Average Diameter        : 2.952 mm
Constriction Time       : 2.983 s
Avg Constriction Velocity : 0.047 mm/s
Max Constriction Velocity : 2.904 mm/s
Max Constriction Amplitude : 0.140 mm
Constriction Ratio      : 95.4%

*Play Debug Movie*

FIG. 5-3A

LEFT EYE
Latency                 : 0.0 ms
Maximum Diameter        : 3.346 mm
Minimum Diameter        : 3.312 mm
Average Diameter        : 3.596 mm
Constriction Time       : 0.100 s
Avg Constriction Velocity : 0.346 mm/s
Max Constriction Velocity : 0.482 mm/s
Max Constriction Amplitude : 0.035 mm
Constriction Ratio      : 99.0%

RIGHT EYE
Latency                 : 0.0 ms
Maximum Diameter        : 2.955 mm
Minimum Diameter        : 2.920 mm
Average Diameter        : 3.191 mm
Constriction Time       : 0.183 s
Avg Constriction Velocity : 0.191 mm/s
Max Constriction Velocity : 0.574 mm/s
Max Constriction Amplitude : 0.035 mm
Constriction Ratio      : 98.8%

*Play Debug Movie*

FIG. 5-3B (a) Light color irides

SYSTEMS AND METHODS FOR OPTICAL EVALUATION OF PUPILLARY PSYCHOSENSORY RESPONSES

CROSS-REFERENCE TO RELATED APPLICATIONS

This application is U.S. National Stage of International Application No. PCT/US2021/013276 filed on Jan. 13, 2021, which claims the benefit of and priority to U.S. Provisional Application No. 62/960,566, filed Jan. 13, 2020, which is hereby incorporated by reference herein in its entirety.

FIELD

The present disclosure relates to systems and methods for optically evaluating psychosensory responses, and more specifically, to systems and methods for measuring and analyzing pupillary psychosensory response.

BACKGROUND

Pupils constrict and dilate in response to various external (e.g., light) and internal (e.g., cognitive/emotional) stimuli. Pupil responses are predominantly evaluated in the context of pupil light response (PLR) for many aspects of physical health using conventional measurement methods such as qualitative measures like clinician-observed penlight or alternative measures like a pupilometer. Pupilometers are expensive, costing as much as $4,500, are mainly used in medical settings, and must be used by a trained clinician. Apart from physical health, pupil responses of an individual can be psychosensory, providing additional information to observers about an internal condition of the individual. That is, pupils not only constrict and dilate in response to external light (as in the case of PLR), but can dilate and constrict in response to cognitive and/or emotional stimuli. Pupil dilation and constriction in response to cognitive and/or emotional stimuli is a pupillary psychosensory response.

SUMMARY

Pupillary psychosensory responses are also difficult to detect, because the resulting percentage change in the pupillary response or pupil diameter is lower compared to the pupil's change in diameter in response to light. Accordingly, conventional pupilometers were previously required to detect a psychosensory response, which would require the patient or user to have access to the pupilometer, and typically would require the patient to be in a health care setting—limiting its applications. Also, these conventional pupil systems are not standardized, require deliberate training, and have poor inter-observer reliability or reproducibility. Furthermore, these conventional systems require one-on-one observations and require (1) proper ambient lighting conditions, (2) proper alignment of face/eyes, (3) sufficient stimulus for pupillary response, and/or (4) adequate processing power for performing external image processing/feature extraction.

Accordingly, systems and methods have been developed for evaluating pupillary psychosensory response using the disclosed image processing techniques that do not require a pupilometer. Thus, these disclosed systems and methods can process image data and detect pupil diameter changes in response to cognitive stimuli. Thus, the systems and methods can be effective for a variety of applications, including detection of lying, detection of cognitive effort, and a variety of healthcare applications (e.g., Alzheimer's disease or other neurodegenerative diseases). Additionally, disclosed herein is data illustrating that the disclosed techniques are effective at evaluating the psychosensory response with surprising accuracy.

According to some implementations, the present disclosure provides an electronic device for evaluating pupillary psychosensory response. The electronic device comprises a processor and a non-transitory computer readable medium with computer-executable instructions stored thereon, such that when the instructions are executed the electronic device is configured to receive video data. The video data includes at least two frames. The electronic device is further configured to locate one or more eye objects in a first frame of the at least two frames and extract, within the first frame, a corresponding iris object for each of the one or more eye objects. The electronic device is further configured to extract, within the first frame, a corresponding pupil object for each of the one or more eye objects. The electronic device is further configured to compute a first set of pupil-to-iris ratios for the one or more eye objects located in the first frame and compute subsequent sets of pupil-to-iris ratios (PIR) for subsequent frames of the at least two frames, each of the subsequent sets of pupil-to-iris ratios pertaining to the one or more eye objects located in the first frame and also in each of the subsequent frames. The electronic device is further configured to determine the pupillary psychosensory response based at least in part on the first set of pupil-to-iris ratios and the subsequent sets of pupil-to-iris ratios.

In some implementations, the electronic device is further configured to locate the one or more eye objects in the first frame using one or more image processing techniques including machine learning, Haar cascades, or deep learning.

In some implementations, the electronic device is further configured to locate one or more face objects in the first frame, wherein each of the one or more eye objects is included in the one or more face objects.

In some implementations, the electronic device is further configured to pre-process each of the one or more eye objects prior to extracting the corresponding iris object and the corresponding pupil object for each of the one or more eye objects.

In some implementations, the electronic device is further configured to crop out each of the one or more eye objects prior to extracting the corresponding iris object and the corresponding pupil object for each of the one or more eye objects.

In some implementations, the electronic device is further configured to crop out the corresponding iris object for each of the one or more eye objects prior to extracting the corresponding pupil for each of the one or more eye objects.

In some implementations, the electronic device is further configured to compute a first set of iris surface areas for each iris object in the one or more eye objects located in the first frame; and the electronic device is further configured to compute a first set of pupil surface areas for each pupil in the one or more eye objects located in the first frame, wherein the first set of pupil-to-iris ratios for the one or more eye objects is computed based on the first set of iris surface areas and the first set of pupil surface areas. Pupil-to-iris ratio as used herein is the ratio of pupil diameter to iris diameter. In some implementations, the one or more eye objects are two or more eye objects belonging to at least two individuals. Surface area as used herein is the area in pixels of the iris or pupil in the frame.

In some implementations, the first set of pupil-to-iris ratios and the subsequent sets of pupil-to-iris ratios indicate a pupil-to-iris ratio trend for a first eye object in the one or more eye objects. The electronic device is further configured to determine the pupillary psychosensory response by determining from the pupil-to-iris ratio trend for the first eye object denoting that an individual to which the first eye object belongs experienced at least one of a cognitive load, effort, stress, sleepiness, memory load, emotion, abnormal/above average neurological processing, or any combination thereof. In some implementations, the pupil-to-iris ratio trend indicates an increase in the corresponding pupil-to-iris ratio during at least a portion of the first frame and the subsequent frames portrays a psychosensory response or a cognitive load of the individual. In some implementations, the electronic device is further configured to receive one or more objective markers that provide additional information and context about the individual; and determine the pupillary psychosensory response further based at least in part on the one or more objective markers in order to provide context and additional information. The one or more objective markers includes one or more of: an acoustic change, a facial flush, a fact check, a physiological response, or any combination thereof.

In some implementations, the electronic device is a smartphone, an augmented reality or virtual reality headset, a television, a computer, or a network of computers. In some implementations, the electronic device further includes a camera configured to receive the video data. In some implementations, the video data is received by the electronic device from an external memory device.

According to some implementations, the present disclosure provides a method for evaluating pupillary psychosensory response. The method includes receiving video data, wherein the video data including at least two frames. The method further includes locating one or more eye objects in a first frame of the at least two frames; extracting, within the first frame, a corresponding iris object for each of the one or more eye objects; and extracting, within the first frame, a corresponding pupil for each of the one or more eye objects. The method further includes computing a first set of pupil-to-iris ratios for the one or more eye objects located in the first frame; and computing subsequent sets of pupil-to-iris ratios for subsequent frames of the at least two frames, each of the subsequent sets of pupil-to-iris ratios pertaining to the one or more eye objects located in the first frame and also in each of the subsequent frames. The method further includes determining the pupillary psychosensory response based at least in part on the first set of pupil-to-iris ratios and the subsequent sets of pupil-to-iris ratios.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The accompanying drawings exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 5-1 shows an example psychosensory response in response to a verbal cue, according to an embodiment of the present disclosure.

FIG. 5-2A shows an example of pupillary response under no cognitive load in a first experimental setting.

FIG. 5-2B shows pupillary response under cognitive load in the experimental setting of FIG. 5-2A.

FIG. 5-3A shows an example of pupillary response under no cognitive load in a second experimental setting.

FIG. 5-3B shows pupillary response under cognitive load in the experimental setting of FIG. 5-3B.

DETAILED DESCRIPTION

Figure 1:
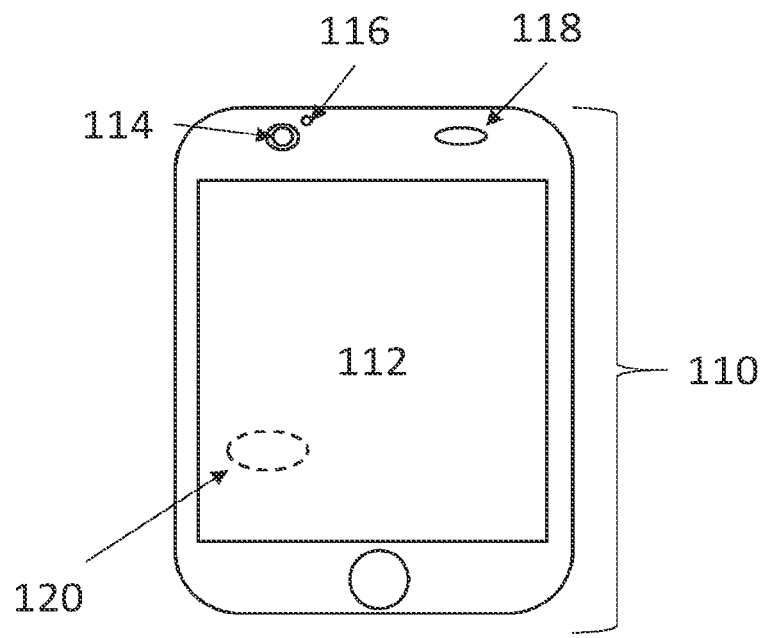
FIG. 1 shows an exemplary system 100, according to an embodiment of the present disclosure.

The present invention is described with reference to the attached figures, where like reference numerals are used throughout the figures to designate similar or equivalent elements. The figures are not drawn to scale, and are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Overview

The present disclosure is directed to systems and methods for capturing and evaluating pupillary psychosensory responses. An exemplary system provides a display and a camera on an electronic device. In some examples, the camera receives video data of pupillary reflex, and the display provides an output interface for a user to observe whether the pupillary reflex is due to a psychosensory response. Therefore, an exemplary device according to the present disclosure provides a scalable (accessible, affordable, and convenient) and accurate (objective and quantitative) system, which can be used by the user in various contexts.

For example, from politicians to chief executive officers (CEOs), people are able to deceive others for their personal gain, without being caught. Current methods for analyzing stress are either qualitative (via a psychologist) or contact-only (via a lie detector machine). Embodiments of the present disclosure provide a non-contact method of analyzing stress responses quantitatively without requiring a user to physically examine the subject. The user can merely obtain video of the subject through any means and analyze the video to determine the subject's stress responses.

Non-contact stress analysis according to some embodiments of the present disclosure can be used in various scenarios. For example, videos of politicians can be analyzed in context to determine whether the politicians are lying about a particular keyword or topic. In another example, public company earnings calls or CEO interviews showing a pupillary psychosensory response consistently on a particular topic or word may help better predict earnings in the next quarter. In another example, casual consumer use is enabled so that a couple, in their home merely using their smartphone, can capture video and audio of each other during conversation in real time. The smartphone can be transformed into a lie detector device, allowing the couple to ask each another questions and determine whether pupillary psychosensory responses present themselves in real-time.

In some examples, the disclosed system includes a smartphone or other handheld computing device. Such a system allows frequent and accurate data collection. In some examples, as discussed further herein, the present disclosure provides for collection of longitudinal health data, which can be used to create baseline pupillary metric measurements for a subject. Therefore, the present disclosure provides measurements that can be specific to certain individuals. For example, some individuals can be very sensitive to light, thus knowing their baseline pupillary metrics can be used to calibrate the disclosed system for more accurate results.

Some examples of the present disclosure further provide for using a non-visible stimulus for image capture. Use of the non-visible stimulus avoids unintentionally stimulating reflexes that adulterate the captured pupillary reflex data. An infrared camera can further provide high-resolution pupil images for effective feature segmentation. The use of infrared light for image capture can be advantageous since the eyes of the subject will not respond to the infrared light. As such, the effect of changes in ambient light affecting the captured pupillary reflex data is eliminated.

Embodiments of the present disclosure thus provide contactless stress examination, providing an examiner with improved access to subjects and allowing the examiner to analyze multiple subjects at once using a computational device. Embodiments of the present disclosure also provide other benefits over conventional methods in that subjects do not need to have a physical test performed on them. Non-contact solutions as discussed in the present disclosure are much more scalable than conventional solutions. There are more publicly available videos of individuals, and specifically, more publicly available videos of CEOs, broadcast personalities, or other public figures for analysis.

Embodiments of the present disclosure take advantage of several technologies not previously available to conventional methods. For example, advent of high resolution video recording in high definition (HD), 4K and above enables extracting features from high quality video at a distance with either commercial grade video cameras or consumer grade video cameras. Furthermore, advances in central processing units (CPUs) and graphical processing units (GPUs) allow for higher resolution video data to be computed and processed in real time. That is, features can be extracted from higher resolution video data in real time. Additionally, advances in artificial intelligence (AI) and neural network software frameworks that leverage increases in CPU/GPU performance allow for more accurate object detection and segmentation. For example, pupil and iris can be identified.

Embodiments of the present disclosure provide a system and method that leverage the aforementioned advancements to obtain psychosensory response metrics, denoising of video data to remove artifacts such as blinks, specular reflections, motion, etc. Embodiments of the present disclosure can accurately evaluate psychosensory responses in commercial applications.

System for Measuring Pupil Metrics

FIG. 1 provides an exemplary system 100, according to an embodiment of the present disclosure. In some examples, system 100 is a smart phone, a smart watch, a tablet, a computing device, head gear, head set, virtual reality device, augmented reality device, or any other device capable of receiving and interpreting a physical signal. System 100 includes a housing 110, a display 112, a camera 114, and a sensor 116. FIG. 1 shows a front side of the system 100.

The housing 110 provides a case for the display 112, the camera 114, and the sensor 116. The housing 110 further includes any computing components (not shown) of the system 100, including, for example, a processor, a memory, a wireless communication element, and any other elements as readily contemplated by one skilled in the art. The computing components further include any software configured to complete any of the processes discussed further herein.

The display 112 is, for example, the screen of a smartphone, a smart watch, an optical headset, or any other device. In some examples, the display 112 is an LCD screen, an OLED screen, an LED screen, or any other type of electronic display, as known in the art, which shows images, text, or other types of graphical display. For example, the screen provides a plurality of light-emitting diodes or other means for generating a plurality of pixels. Each pixel displays a light stimulus. In some examples, the pixels function independently, each providing a different light stimulus from the other pixels; in other examples, the pixels function cooperatively to provide a coordinated light stimulus. In some examples, some of the pixels function cooperatively, and some operate independently.

The display 112 is configured to emit visual light. In some examples, the display 112 emits light on a portion of a surface area of the display 112; in other examples, the display 112 emits light on all of a surface area of the display 112. The light emitted by the display 112 can be controlled to automatically emit light, and increase or decrease the visible stimulus. In some examples, the display 112 shows image data and/or video data captured by the camera 114.

The camera 114 receives video data of a field of view in front of the camera 114. In some examples, the camera 114 receives photographic and/or video data. In some examples, the camera 114 receives continuous photographic data (e.g., at intervals of seconds, milliseconds, or microseconds). In some examples, the camera 114 is a visual light camera. In some examples, the camera 114 is an infrared camera. In some examples, the camera 114 automatically initiates image data capture based on detecting certain stimulus (for example, a face of a user, an eye of a user, a pupil of a user, and/or an iris of a user).

The sensor 116 includes, for example, any of a light sensor, an ambient sensor, and/or an infrared sensor. In some examples, the sensor 116 is communicatively coupled to the camera 114 and is configured to initiate and/or terminate image data capture by the camera 114. As shown, the sensor 116 is on the same side of the system 100 as the camera 114. In some examples, the sensor 116 is placed proximally close to the camera 114.

Figure 2:
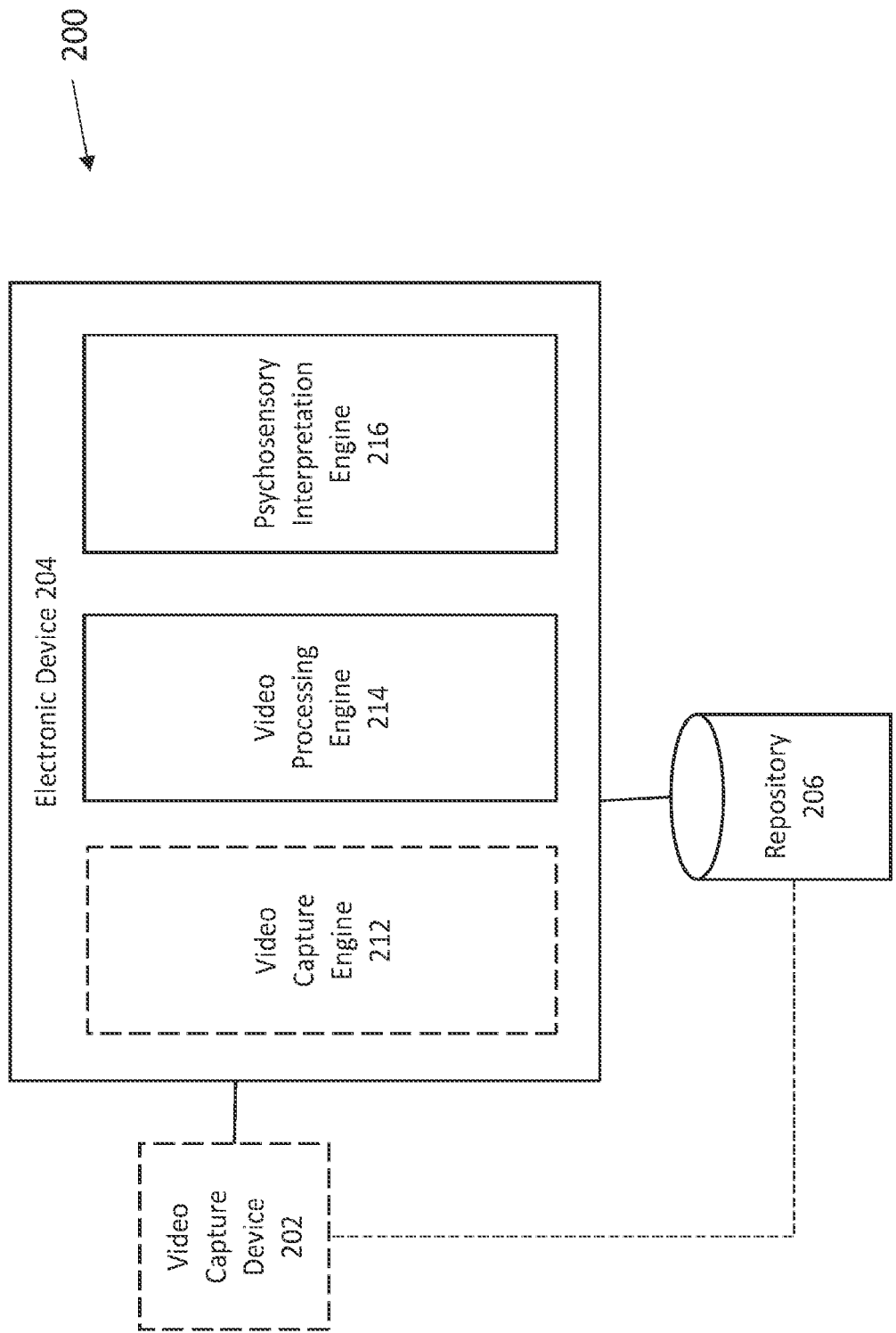
FIG. 2 shows an exemplary system 200 for measuring pupillary response, according to an embodiment of the present disclosure.

In some examples, the sensor 116 includes a microphone for capturing sound such that image captured by the camera 114 can be correlated with sounds. In some examples, the system 100 includes touch sensors 120 as part of the display 112. In some examples, the system 100 includes a speaker 118 for playing sounds. FIG. 1 shows a specific system implementation where components are integrated in a single housing. FIG. 2 generalizes the system 100 of FIG. 1 in that, the captured video and sound can come from an external memory or can be captured by the camera 114.

FIG. 2 shows an exemplary system 200 configured to receive video of one or more subjects and process psychosensory responses according to some implementations of the present disclosure. The system 200 can include a video capture device 202 for capturing video. The video capture device 202 can be an external camera that captures video. The video capture device 202 can provide the captured video to an electronic device 204 for processing, or the captured video can be stored in a repository 206. The system 200 includes the electronic device 204 and can include the repository 206. The repository 206 stores data and other parameters that the electronic device 204 can use in processing data. The repository 206 can be distributed in multiple locations such that the electronic device 204 can retrieve captured video data from one or more of these locations. That is, the electronic device 204 can access online videos stored in the repository 206 or can receive video in real-time (e.g., a web conference or video call).

In some implementations, the electronic device 204 can include a video capture engine 212. An engine is a combination of hardware and software configured to perform specific functionality. The video capture engine 212 can be a camera and memory internal to the electronic device 204. For example, the camera 114 in the system 100 captures and stores video data in the system 100, thus performing functions of the video capture engine 212. The electronic device 204 can store captured video in the video capture engine 212 or can store the captured video in the repository 206.

The electronic device 204 further includes a video processing engine 214 for extracting features in the captured video. For example, the captured video can be stored in the video captured engine 212, in the repository 206, or can be received from the video capture device 202. The video processing engine 214 can include one or more CPUs and/or GPUs for extracting features in the captured video. For example, the video processing engine 214 can process the captured video to identify and isolate faces of the one or more subjects, irises of the one or more subjects, and pupils of the one or more subjects.

The electronic device 204 further includes a psychosensory interpretation engine 216 for determining whether the one or more subjects are experiencing psychosensory responses over a period of time. The psychosensory interpretation engine 216 takes measurements of the iris and pupils from the video processing engine 214 and determines from changes in the measurements whether the one or more subjects are experiencing psychosensory responses over the period of time. The psychosensory interpretation engine 216 can use one or more sensors to determine objective markers that provide additional information and context about the one or more subjects. The objective markers can include an acoustic change, a facial flush, a spoken word, a fact check, a physiological response, or any combination thereof. The psychosensory interpretation engine 216 can use sound cues associated with image frames in the captured video to determine the psychosensory responses. The psychosensory interpretation engine 216 can use lighting cues to rule out psychosensory responses in the event ambient light may be more attributable to a pupillary reflex.

The system 200 can use visual cues to objectively measure a subject's psychosensory response. Pupil dilation is controlled by the autonomous nervous system, the same system that controls heart rate and the same system lie detectors monitor. By identifying changes in pupil diameter, the system 200 can identify psychosensory autonomic stimuli, such as but not limited to, stress, cognitive load, effort, memory load, emotion, abnormal/above average neurological processing, and sleepiness. The system 200 can be applied to an abundance of high resolution videos of public and private figures to objectively quantify their levels of stress, cognitive load, effort, and sleepiness in connection with words, terms, ideas, or topics of discussion. For example, the system 200 can calculate pupil-to-iris ratio over the time the public figures are speaking publicly and then provide an index that shows when there are deviations to the baseline pupil-to-iris ratio. The system 200 can correlate the index with other objective markers, such as but not limited to, acoustic changes, facial flush, or even fact-checking. If the deviations indicated by the index show up at the same exact time in a video via these other methods, the system 200 can corroborate a correlation and confirm that the speaker is undergoing a pupillary psychosensory response, and/or that the speaker is potentially lying/stressed.

Methodology for Analyzing Pupil Response

In some embodiments, the smartphone may not only capture the phenotypic data showing pupillary dilation and constriction, but also process the data locally and in real-time. Similarly, other quantifiable feature extractions measured from the eye/face (such as sclera color and deposit density) might also be processed locally. The method and system may also allow for the calculation of dynamically changing diameter of pupil. The method and system may generate a more robust baseline upon which to detect real-time detect statistical deviations. Such deviations may indicate an anomaly in a subject, especially when the subject is undergoing cognitive stress or other neurological processes.

The psychosensory response measurements described herein can be temporally and spatially coupled with other measures including, but not limited to: the voluntary reflex of a user's blink speed in response to the verbal cues or while the user is reading. Cognitive effort when reading and understanding can affect blinking in that blinking is neuronally processed through the motor cortex to then result in a measurable blink of the eye or eyes (which could be a measure of physiologic changes taking place in the voluntary nervous system pathway). These features, which can be efficiently measured within spatial and temporal proximity by a user, can be quantitatively and longitudinally (throughout time) measured and baseline-established on an individual basis convenient, affordable, and accessible from a users' life setting (e.g. home, or non-medical). Such data may generate insights into various physiologic systems (e.g. neuro, cardio, etc.).

Psychosensory response is determined by examining video (or at least two frames) of a subject. In some implementations, the subject's eyes are identified. Then computer vision image processing is used to identify shapes (or approximately circles) defining the iris and pupil boundaries. Then the ratio of the diameters of the pupil circles and the iris circles is computed. This ratio is monitored for changes over time. An increase in the ratio from the baseline portrays a psychosensory response of the subject.

In some embodiments, the iris diameter (which does not change) is used as a normalizer (i.e., used in the denominator to normalize any pupil diameter measurements) because it allows referencing the pupil change against iris. This normalization is helpful when a subject may be moving to/from the camera (i.e. there is a fixed reference and the ratio between the pupil diameter and the iris diameter is a unitless value as a function of time).

Figure 3:
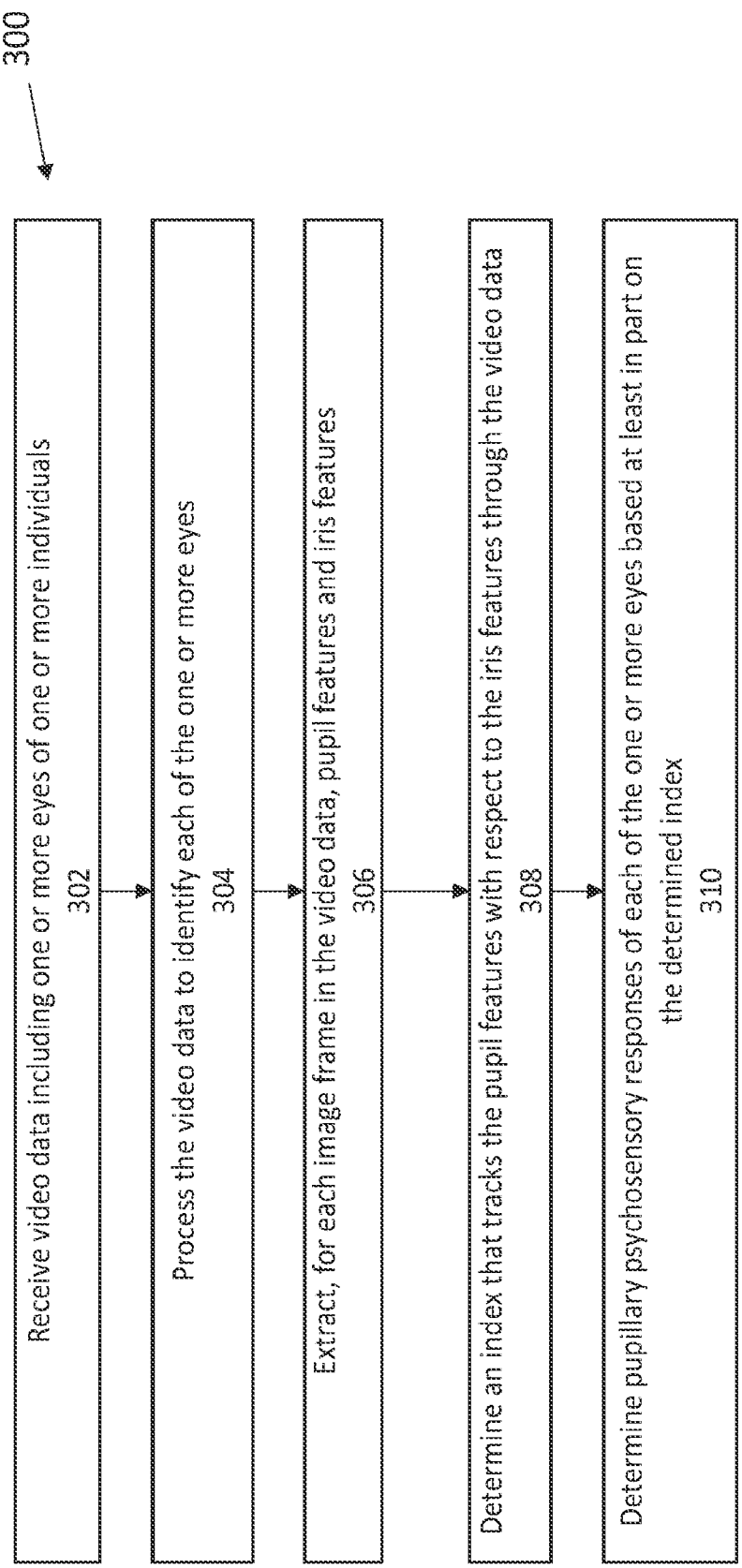
FIG. 3 shows an exemplary methodology 300 for evaluating pupillary psychosensory responses, according to an embodiment of the present disclosure.

FIG. 3 shows an exemplary methodology 300 that can be performed according to the various embodiments of the present disclosure. Methodology 300 can be performed on systems 100 and 200 as discussed with respect to FIGS. 1 and 2.

Methodology 300 begins at 310 by receiving video data including one or more eye objects of one or more individuals. A video is made up of at least two image frames, and an object is a recognizable entity visually represented on a portion of a frame. For example, an eye object is an eye visually represented on a portion of one or more frames of the video. As discussed in connection with FIG. 2, the video data received at 310 can be received from the video capture device 202, can be captured by the video capture engine 212, can be retrieved from the repository 206, or can be retrieved from an internal storage or memory of the electronic device 204. The one or more eye objects can belong to one or more subjects. That is, the received video data can include multiple individuals in each frame of the video data.

Methodology 300 then provides for processing the received video data to identify each of the one or more eye objects. The video processing engine 214 can locate the one or more eye objects in each frame of the video data. The video processing engine 214 can tag each of the located one or more eye objects such that a respective eye object can be tracked sequentially from one frame to another throughout the video data. The video processing engine 214 can apply image processing techniques, machine learning techniques, deep learning techniques, etc., to locate the one or more eye objects. For example, the video processing engine 214 can use machine learning, Haar cascades, deep learning, or any other classifier to identify the one or more eye objects in each frame of the video data.

In some examples, the video processing engine 214 locates one or more face objects in each frame of the video data. And from the one or more face objects, the video processing engine 214 only tracks the one or more eye objects contained within the one or more face objects. That is, the video processing engine 214 first locates faces and then identifies eyes within the located faces and these are the eyes that are being tracked.

Methodology 300 then provides for extracting from the video data pupil features and iris features. Features is used broadly in that, the video processing engine 214 merely extracts pupil objects and iris objects for the one or more eye objects identified. Features can include color, shape, texture, distinguishing marks, etc. In some implementations, iris features are not extracted, and only pupil features are extracted.

In some examples, prior to extracting the pupil features and iris features, the video processing engine 214 determines that only a certain number of located eye objects include enough detail for further processing. As such, the video processing engine 214 can discard and stop tracking one or more eye objects. The video processing engine 214 can also prune and combine results to keep eye objects with the best resolution after identifying each of the one or more eye objects.

In some examples, the video processing engine 214 can crop and preprocess each of the one or more eye objects. Exemplary types of data pre-processing are discussed further below. Cropping the one or more eye objects allows for a narrower focus and can save computational power so that an entire frame is not being processed by the video processing engine 214 but only areas of interest (which in this case are the eye objects).

In some examples, the video processing engine 214 computes edges to find an iris object of an eye object and can then further crop the iris. After finding the iris object and further reducing image area to be processed through the cropping of the iris, the video processing engine 214 can compute edges to find a pupil object associated with the found iris object. Results can be further pruned to keep best proposed pupil objects found. For example, the video processing engine 214 can make best guesses of the boundary of the pupil object throughout the video data. The video processing engine 214 can come out with different answers based on a resolution of the image frames being worked with. The video processing engine can then combine the different guesses via an average or a smoothing function to remove outliers.

Methodology 300 then proceeds to determine, for each of the one or more eye objects, an index that tracks the pupil features with respect to the iris features or distance throughout the video data. Since the video data can include a subject that moves around and does not necessarily make eye contact with the camera all the time, the index should be able to provide actionable information whether or not the subject is moving. A subject that moves towards the camera will appear to have larger iris and pupil, and as the subject moves away from the camera, the iris and the pupil will appear smaller.

In some examples, a baseline pupil diameter can be determined based on the distance from the camera. This would be based on, for instance, an infrared depth sensor on smartphone or the presence in the video of a physical reference object near the face. Knowing the distance from the camera and using this distance as reference, the physical diameter of the pupil can be calculated, thus any changes to the diameter can be referenced back to the distance from the camera. The pupil diameter (e.g., measured in millimeters) can serve as the index in these examples and the iris measurements are not necessary.

In some examples, a pupil-to-iris ratio is determined as the index. The iris object and the pupil object can be approximated as concentric circles. A surface area of the circles can be determined such that the ratio can be expressed as a diameter of the pupil object divided by a diameter of the iris object. In some implementations, the ratio can be a squared value to retain the area comparison of the pupil object with respect to the iris object. The pupil-to-iris ratio can be determined for each of the frames in the video data.

In some examples, frames where the subject is not looking at the camera are removed. That way, memory usage can further be decreased.

In some examples, 308 further provides for determining a surface area of pupil and iris regions, as detected in the image data. For example, imaging analysis software algorithms determine pupil size parameters across a series of recorded images by evaluating the elapsed time between each image to determine the rate at which the pupil size changes over time.

Methodology 300 then proceeds to determine, at 310, pupillary psychosensory responses of each of the one or more eyes based at least in part on the determined indexes of 308. By discounting change in ambient light, etc., the psychosensory interpretation engine 216 can determine whether the subject has experienced or is experiencing a cognitive effort, stress, sleepiness, interest, drug use, dementia, depression, anxiety, behavior disorder, or any combination thereof. An increase in the index over a period of time indicates that the subject is undergoing some sort of stress. The psychosensory interpretation engine 216 can correlate the stress over the period of time to one or more objective markers pertaining to the subject. For example, the subject can be affected by a verbal cue which can cause the speaking subject to undergo an acoustic change, or cause the subject to experience a facial flush. In another example, the subject can be affected by a visual cue which can cause similar responses.

Although the index or indexes are described as ratios, the ratios can be tracked over time to determine a trend. For example, further analysis of the index over multiple frames of the video data can provide additional information including: (1) pupil response latency, which includes the time taken for a pupil to respond to a verbal cue, for example, in milliseconds; (2) maximum diameter, which is the maximum pupil diameter observed; (3) minimum pupil diameter, which is the minimum diameter observed; (4) dilation velocity, which is the average velocity observed over the total dilation period; (5) average diameter, which is an average of all diameter measurements taken in a time series; (6) pupil escape; (7) baseline pupil amplitude; (8) maximum pupil diameter; (9) any other pupillary response measurements, as known in the art; and (10) any combination thereof. Each of the aforementioned measurements can be normalized to the diameter of the iris as previously discussed.

For example, pupillary response latency can be a dilation response latency (or a constriction response latency). Dilation response latency is measured as dilation($t_{verbal\_cue}$)−dilation($t_{intial}$) For example, dilation velocity is a measure of the rate at which the pupil dilates in units of iris diameter/second. For example, dilation amplitude is measured as (Diameter$_{min}$ prior to a verbal cue)−(Diameter$_{max}$ following the verbal cue). For example, dilation percentage is measured by taking the dilation amplitude as a percentage of Diameter$_{min}$. For example, dilation velocity is a measure of the rate at which the pupil dilates in millimeters/second. Many of the features listed above can be derived by evaluating the diameter of the pupil at a first image, the diameter of the pupil at a second image, and a length of time between the two images, as would be readily contemplated by a person skilled in the art. Furthermore, a person skilled in the art would readily understand that constriction latency, constriction velocity, constriction amplitude, and constriction percentage can be similarly calculated based on the data provided at 306.

In some examples, a trend may be analyzed using various models. These models may include, but are not limited to, decision trees, linear regression, random forest, or logistical regression models. In addition, a trend may be determined using various other machine learning models, including supervised machine learning models trained with data from patients with and without a particular medical condition.

In some examples, the system may establish a baseline amplitude in cognitive response based on a measure of diameter for the first 5, 10, 15, 20, 30, 40, 50, or 60 seconds, or other suitable time frames, and identify a stimulus that deviates from the baseline in frames captured after the baseline.

In some examples of methodology 300, the video data includes data of both eyes of a subject. At 306, each pupil's reflex is analyzed separately; but, at 310, the features of the two are analyzed together to determine pupillary psychosensory responses.

Example Pupil Response Curves

Figure 4A:
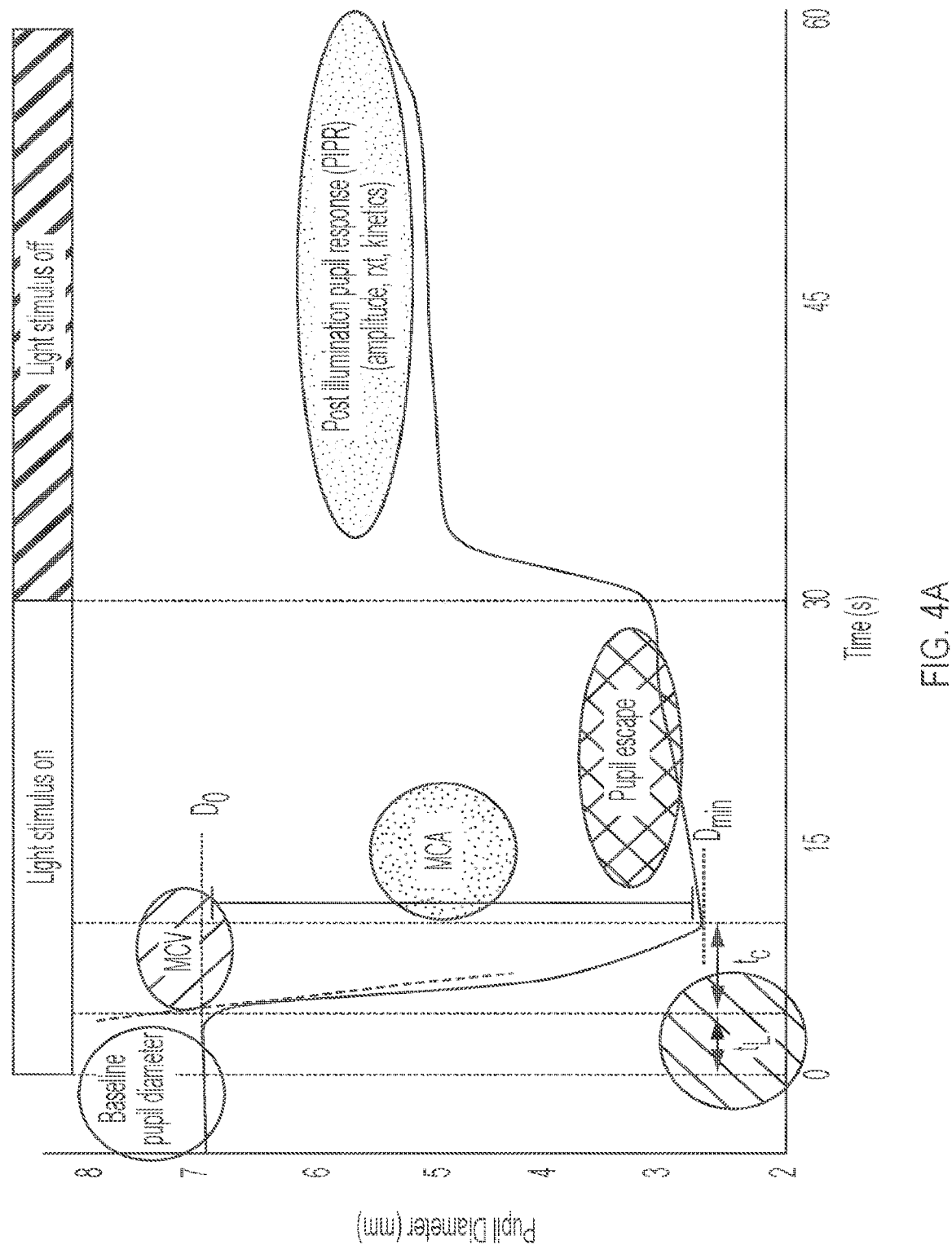
FIG. 4A shows an exemplary pupillary response separated into sub-phases, according to an embodiment of the present disclosure.

Pupils are known to respond to ambient light, as such, changes in ambient light can effect a change in pupil diameter. FIG. 4A shows an exemplary pupil response curve and the various features that can be identified at different points in the curve. FIG. 4A demonstrates that when a light stimulus is on, a baseline pupil diameter is first detected; MCV, MCA, and pupil escape are subsequently evaluated. When the light stimulus is turned off, a post-illumination pupil response (PIPR) can be evaluated.

Figure 4B:
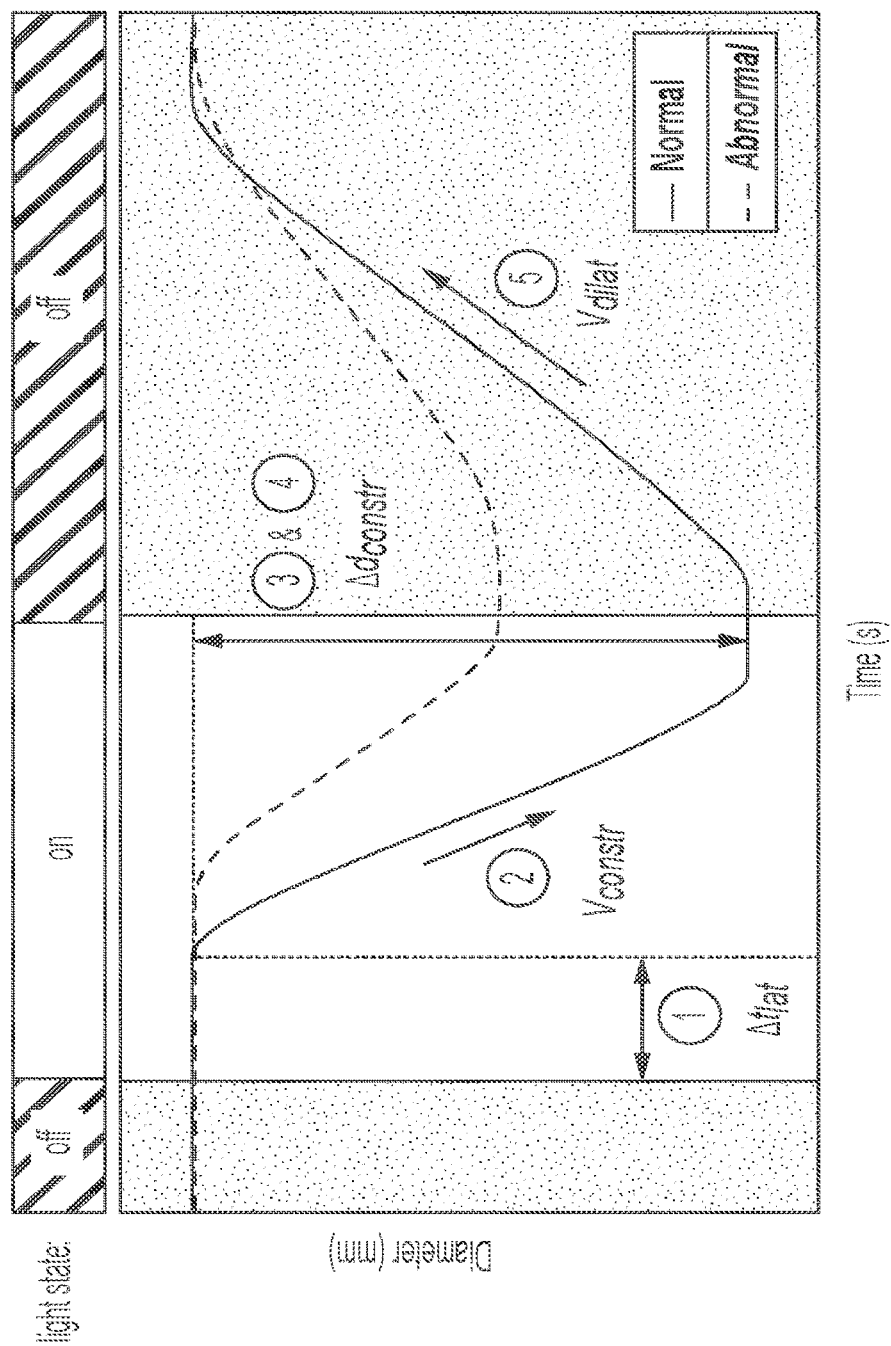
FIG. 4B shows exemplary pupillary responses as compared between a healthy and unhealthy subject, according to an embodiment of the present disclosure.

FIG. 4B shows another exemplary pupillary light reflex (PLR) curve, including: (1) latency, (2) constriction velocity, (3) constriction amplitude, (4) constriction percentage, and (5) dilation velocity. The dashed line shows an abnormal PLR curve with increased latency, slower velocities, and diminished amplitude than the normal PLR curve shown by the solid line.

Although FIGS. 4A and 4B show pupil responses to light, similar effects are observed when a subject is under cognitive stress. As such, the pupil dilates when under cognitive stress and constricts when the cognitive stress is absent. Analogous to introducing a light stimulus, a cognitive stimulus can be provided to a subject. A baseline can be measured at constant lighting, prior to providing the cognitive stimulus. The cognitive stimulus can then be provided to observe pupil dilation from the baseline. The pupil can then return constrict to a smaller diameter once the subject stops considering the cognitive stimulus.

Experimental Results

Figures 1, 5:
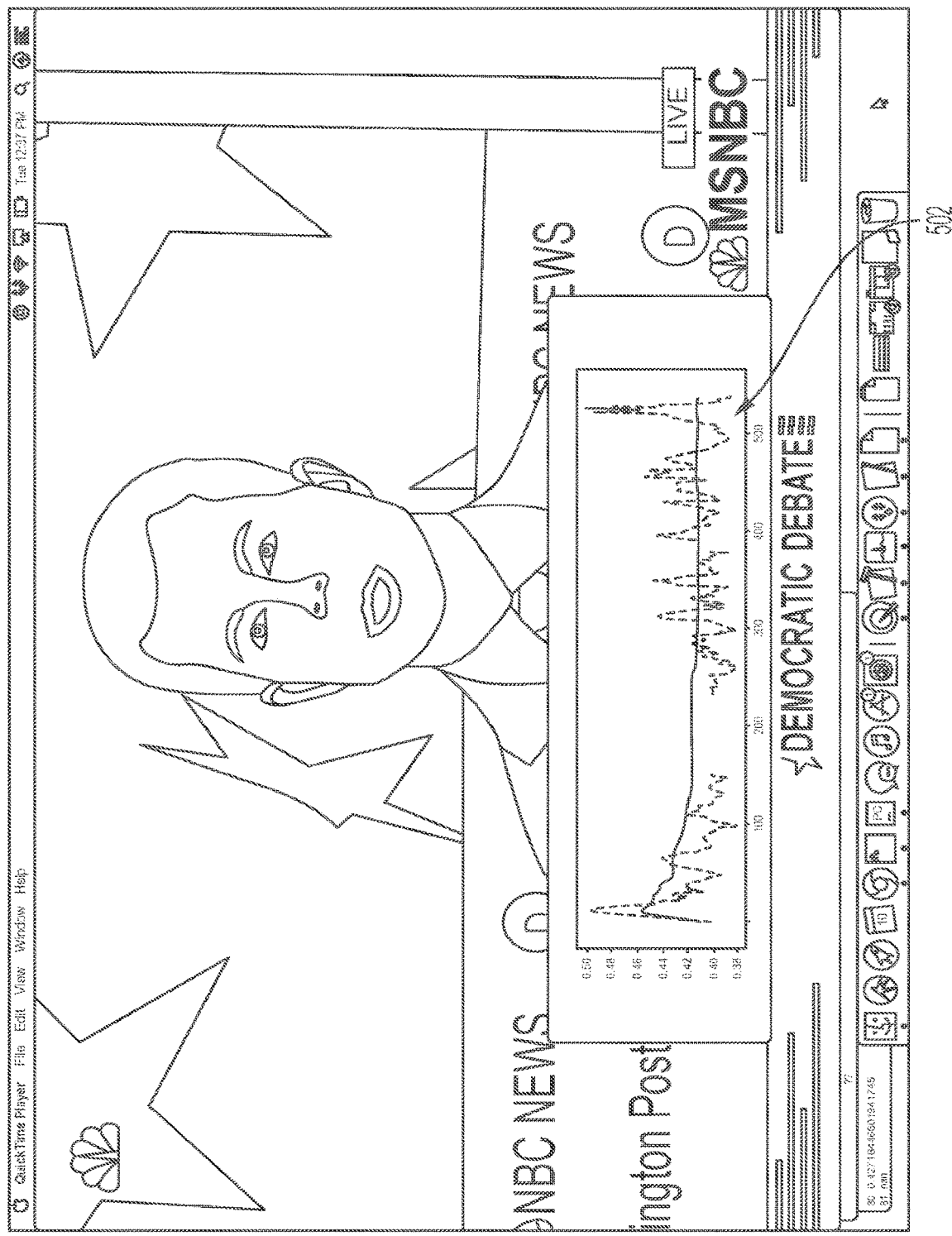

FIG. 5-1 shows example experimental data for evaluating pupillary psychosensory response using an index determined as the pupil to iris ratio of someone in a high stress situation. The plot 502 provides the index as a function of time. As the subject listens and begins answering the question (left side of plot), the subject has a psychosensory response, likely due to the stress and cognitive effort involved in thinking and answering a question with millions of people watching. Furthermore, there is a general return to baseline values when the stress subsides. In this example, the subject receives multiple internal stimuli which can be observed externally with no physical contact.

FIGS. 5-2A and 5-2B show example experimental data for evaluating pupillary psychosensory response according to some implementations of the present disclosure. In FIG. 5-2A, a subject was told that a math problem would be provided to him and that he would have three seconds to mentally calculate a solution to the math problem. As can be seen in FIGS. 5-2A, pupillary response of the right and left eyes first trend downward such that the pupils constrict, then from about T=2, pupillary response mostly hovers around 3.75 mm for the left eye and 3.06 mm for the right eye. In FIG. 5-2B, the subject was told to mentally perform 7×7×7. In FIG. 5-2B, both the left and right eyes dilate such that pupillary response trends upward until about T=3.5.

FIGS. 5-3A and 5-3B show similar experimental examples as FIGS. 5-2A and 5-2B, respectively. FIG. 5-3A is a baseline where no cognitive load is present, and the subject merely prepares to receive a mental question. FIG. 5-3B shows that both the left eye and the right eye dilate in response to receiving a question at T=0.

Pre-Processing & Processing the Data

In some examples of 302 and 306, the received image data is pre-processed. Exemplary pre-processing techniques are discussed herein.

Video data including image frames in sequence can be smoothed to de-noise the system of natural fluctuations in the pupil, as well as variance caused by changes in ambient light. A Gaussian smoothing operator can be used to slightly blur the images and reduce noise. The 2D Gaussian equation has the form:

$$G(x, y) = \frac{1}{2\pi\sigma^2} e^{\frac{-(x^2+y^2)}{2\sigma^2}} \quad \text{Equation 1}$$

where sigma is the standard deviation of the distribution, which may be given by:

$$\sigma = \sqrt{\frac{1}{N} \sum_{i=1}^{N} (x_i - \mu)^2} \quad \text{Equation 2}$$

where x is the $i^{th}$ pupil reflex measurement, μ is the mean pupil reflex measurement, and N is the total number of pupil reflex measurements.

In some examples of the present disclosure, pupil dilation and contraction under cognitive stress can be represented as smooth Fourier transformations. For example, when using a histogram representation of the smoothed grayscale frames, a threshold function binarizes the images. This threshold function can be determined by the distinction between dark and light pixels on the histogram. Based on this, the images can be binarized in such a way that distinguishes the sclera from the pupil by labelling white parts of the image with a 1, and black parts of the image with a 0. This effectively generates a black square with a white circle representing the pupil clearly for analysis. Pupils are generally shaped as ellipses, but can be represented as a circle by averaging the axes. Diameter can be measured in pixels between the two white pixels farthest away from each other. This pixel measurement can be converted to millimeters using a fiducial of known dimensions held near the eye. For example, depth of the smartphone from the face might be determined using a dot projector in a smartphone.

In some examples, pre-processing includes cropping the footage to include a region of each individual eye. This can be implemented by applying the simple heuristics of the known structure of the human face. The footage can then be submitted for processing, which includes, for example, deconstructing the received visual stimulus into a series of images to be processed one by one. Images are manipulated to eliminate the aberrations of eye glasses, blinking and small hand movements during image capture. Pupil boundary detection using entropy of contour gradients may be used to extract the size of each pupil and create data series which could be visualized.

In some embodiments, a camera may be used to capture frames of eyes with different levels of dilation. The user can manually tag the pupil diameters for each frame. Using the tagged data, a segmentation or detection model can be trained using the tagged pupils. For example, U-Net or an analogous service might be used to output shapes from which diameter may be inferred. A pipeline may be implemented to process recorded frames of video and graph the pupil dilation over time.

In some examples of processing the data, hue, saturation, and brightness values are used to filter the received image data. For example, pixels may be filtered out if the pixels have a "V" value (which represents brightness) of greater than 60. In another example, the pixels may be filtered based on LAB values, where "L" represents a brightness of the pixel, and "A" and "B" represent color-opponent values. Because the pupil is the darkest feature of the eye, pixels may be filtered out which have an "L" value greater than 50, thereby leaving only the pixels which are relatively darker and more likely to include the pupil. Preprocessing methods provided here are merely examples. Other preprocessing methods can be used as needed, for example, grayscale morphological filtering can be used to minimize specular reflection artifacts.

Additional exemplary processing steps include (1) duplicating the filtered image, discarding what has been filtered out to just show the region of interest (ROI), (2) converting the filtered ROI pixels to grey scale, (3) filtering grey scale pixels based on brightness or intensity values, for example, by filtering pixels having an L value higher than 45, (4) scanning the remaining pixels for contours and convex shapes, (5) scanning the pixels for incremental gradients in grey scale values of pixels, (6) constructing shapes based on, or defined by, the contours, (7) filtering those shapes based on size and circularity, (8) determining a surface area of pupil region and iris region, and (9) determining a relative change in the two regions over time.

In some examples of filtering based on circularity, the device filters out values which are not at or around a 1.0 circularity value. For example, circles have circularity values at or near 1.0, while an elongated ellipse may have a circularity value of around 0.25.

Predicting Psychosensory Response Based on Pupil Features

Figure 6A:
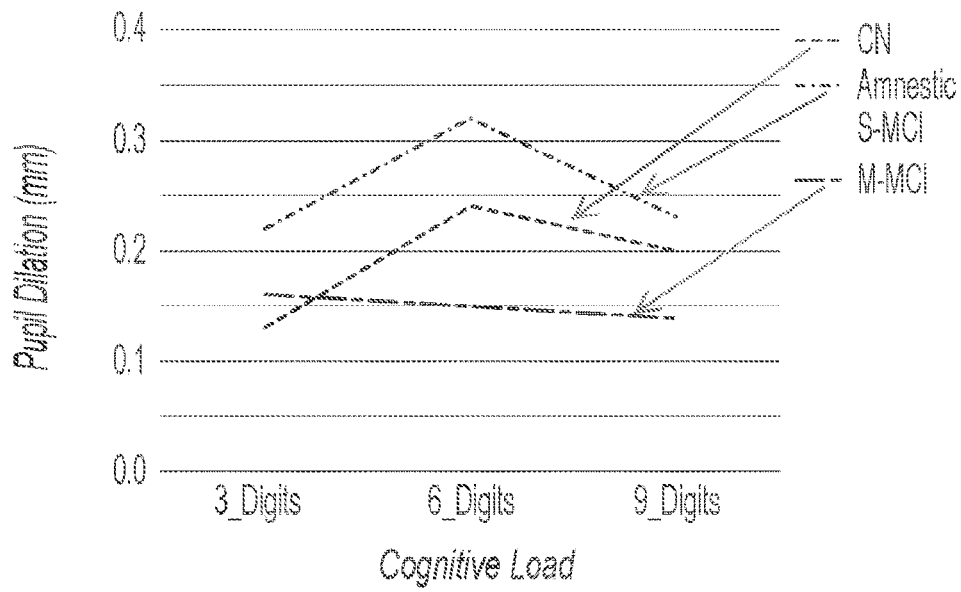
FIG. 6A shows exemplary pupillary responses to cognitive load, according to an embodiment of the present disclosure.
Figure 6B:
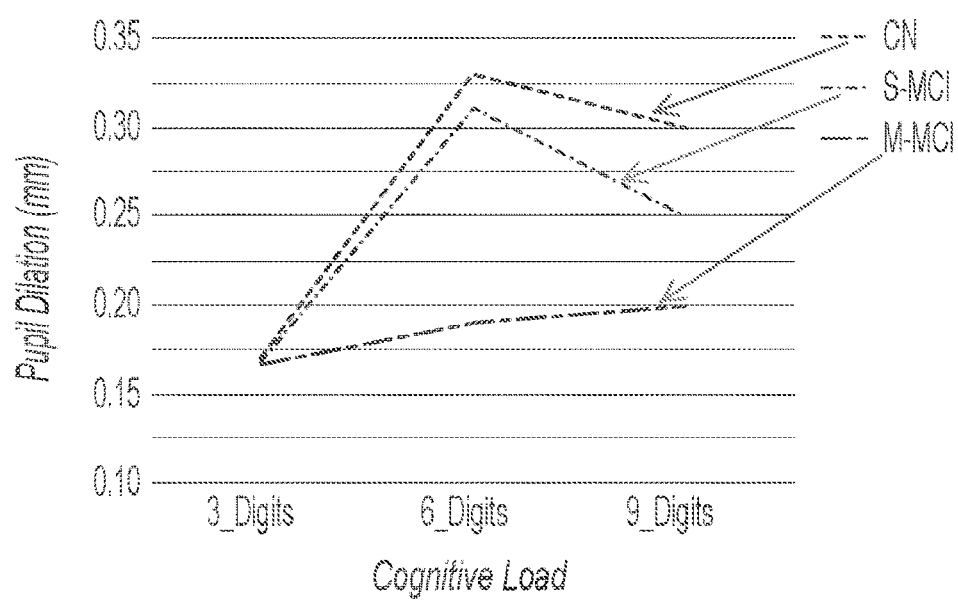
FIG. 6B shows exemplary pupillary responses to cognitive load, according to an embodiment of the present disclosure.
Figure 7:
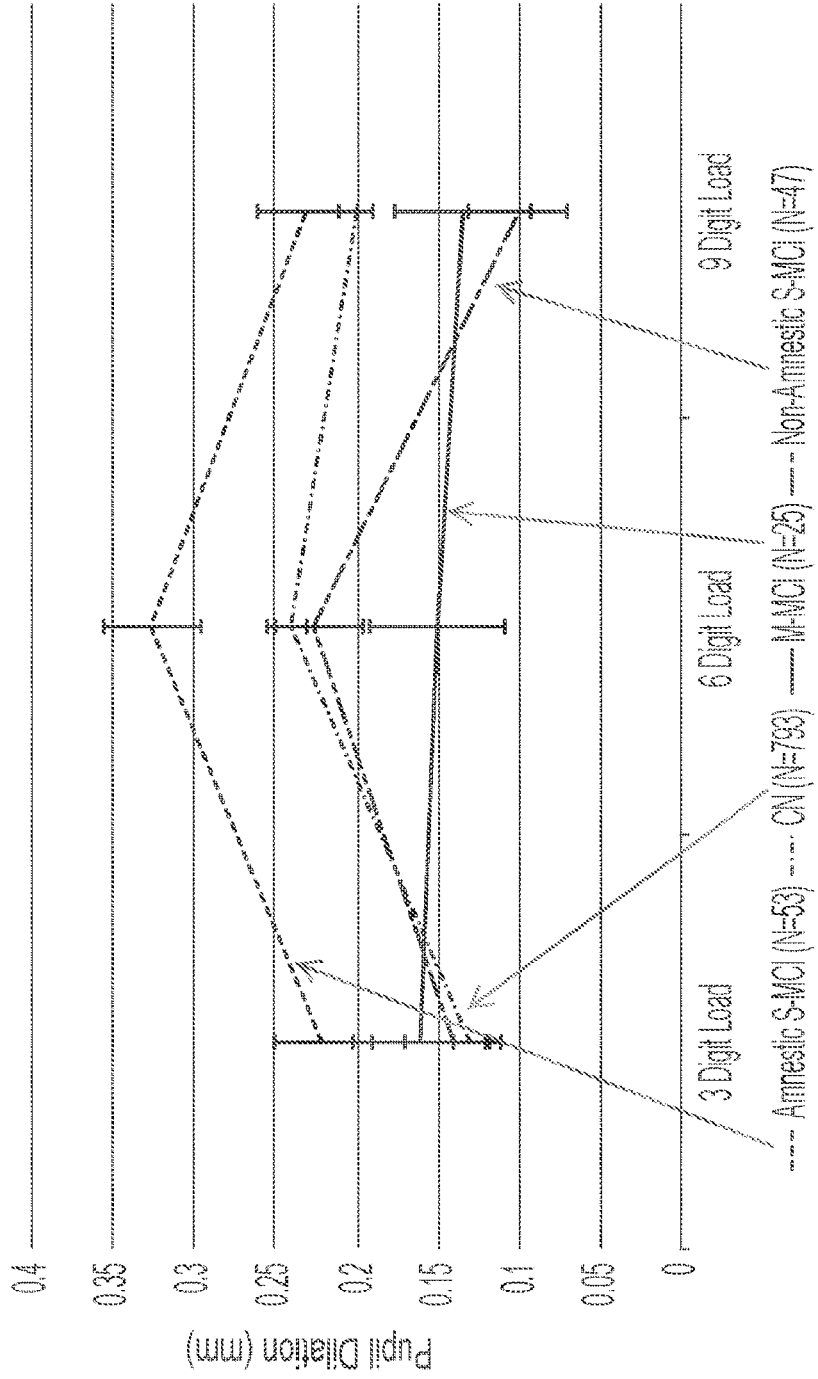
FIG. 7 shows exemplary pupillary responses as a function of mild cognitive impairment, according to an embodiment of the present disclosure.

Various aspects of methodology 300 of FIG. 3 can be used to evaluate whether a subject is experiencing a psychosensory response. Subjects can have different pupillary responses based on damage to cognition, as such, subjects can be at different baselines. FIGS. 6A, 6B, and 7 below demonstrate exemplary data that corresponds to pupillary responses under different cognitive loads for different types of individuals.

FIGS. 6A-6B show exemplary pupillary responses to cognitive load, according to an embodiment of the present disclosure. FIGS. 6A-6B demonstrate that the psychosensory pupil response and Alzheimer's Disease are correlated. Cognitive load is measured by whether a subject can recall spans of 3, 6, or 9 digits. FIGS. 6A-6B demonstrate that with increased cognitive load, the amnestic single-domain mild cognitive impairment (S-MCI) group showed significantly greater pupil dilation than a cognitively health control group (CN). Furthermore, at certain cognitive loads, the multi-domain mild cognitive impairment (M-MCI) group showed significantly less dilation than both the cognitively normal and S-MCI groups. This indicates a cognitive load well beyond the capacity of the group.

FIG. 7 shows exemplary pupillary responses as a function of mild cognitive impairment, according to an embodiment of the present disclosure. For example, this data shows pupil dilation increases in response to a 6-digit load from a 3-digit load, but decreases once capacity is reached at a 9-digit load. Therefore, the present disclosure contemplates that individuals with lower cognitive ability would show greater pupil dilation under lower loads and less at higher loads. These results can help indicate whether a speaker is actually considered a question being asked or whether the speaker is merely reciting already learned material.

Pupil Segmentation

Pupil and iris diameters can be measured directly without formal segmentations, but in some implementations, pupil segmentation methods can be used prior to measuring pupil and iris diameters. The image data of the eyes can be segmented into three main parts: pupil, iris, and sclera. Image Segmentation Algorithms can be used to provide a desired segmentation.

Figure 8:
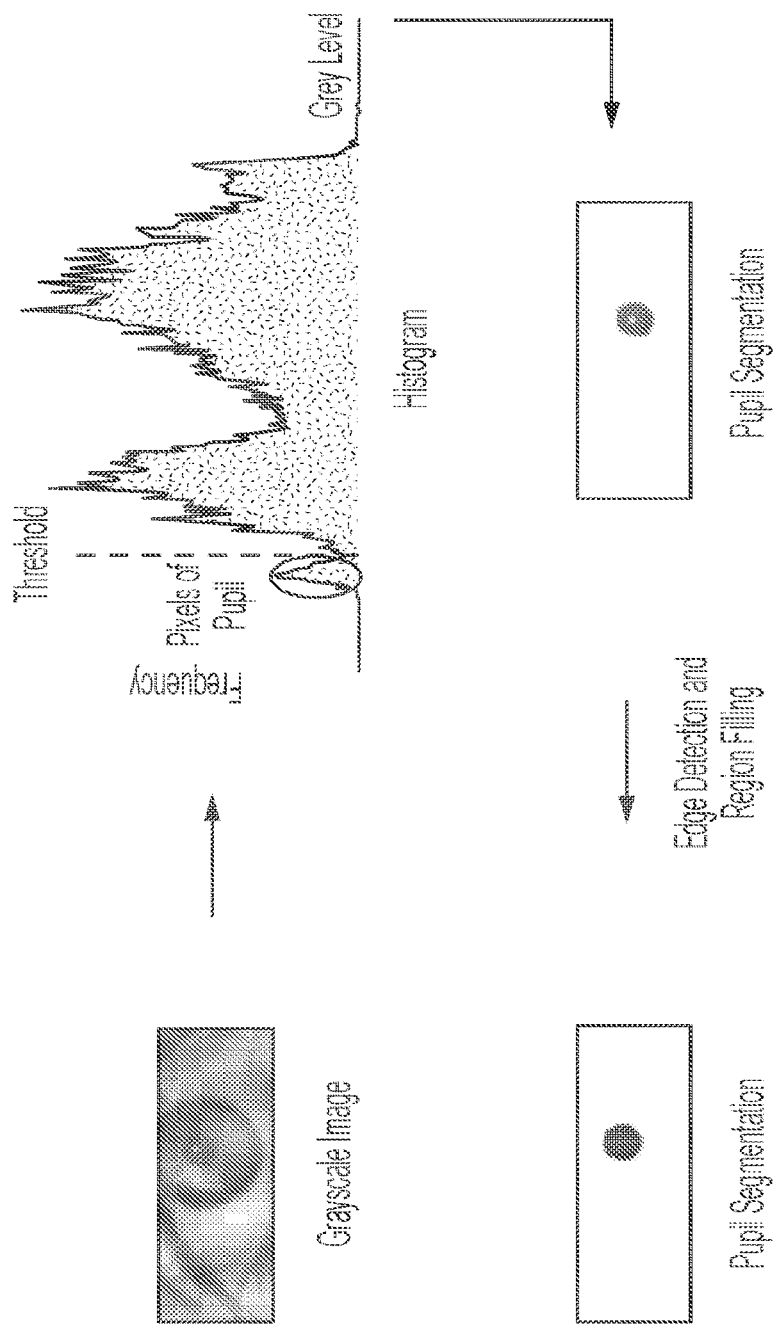
FIG. 8 shows an exemplary pupil segmentation methodology, according to an embodiment of the present disclosure.

FIG. 8 shows an exemplary pupil segmentation process. First a greyscale image of an eye is received. Then, a balanced histogram is created based on a grey level of each of the pixels. For example, balanced histogram thresholding segmentation, K-means clustering, or edge detection and region filling might be used. An exemplary balanced histogram segmentation algorithm sets a threshold grey level for the pixels to determine which correspond to the pupil. The pixels corresponding to the pupil will be the darkest pixels.

In one example, K-means clustering chooses k (e.g., k is 4 in this example) data values as the initial cluster centers. The distance between each cluster center and each data value is determined. Each data value is assigned to the nearest cluster. The averages of every cluster are then updated and the process repeated until no more clustering is possible. Each cluster is analyzed to determine which cluster includes the pixels of pupil, getting the segmentation result. This method can be used to segment the interest area from the background based on the four main parts in the eyes having different colors: black pupil, white sclera, colored iris and skin background.

The method shown in FIG. 8 further provides for edge detection and region filling, which enhances the image and links the dominant pixels of the pupil. Holes of certain shapes and sizes are filled to get the final results of segmentation. Edge detection and region filling are not necessary in pupil segmentation since only the diameter of the pupil is of interest, hence the last step shown in FIG. 8 can be skipped.

After segmentation, the area of the pupil is determined, measured in pixels. In some implementations, this pixel measure is converted to a physical size (e.g. millimeters) based on a scale of the camera which collected the image data. In some implementations, a normalized pixel measure is provided where diameter of the pupil is normalized to diameter of the iris. As such, even when camera angles change or camera zoom changes, the normalized ratio between the pupil and iris will not be distorted by the changes to the physical properties of the camera.

Measuring Pupil Diameter

Figure 9:
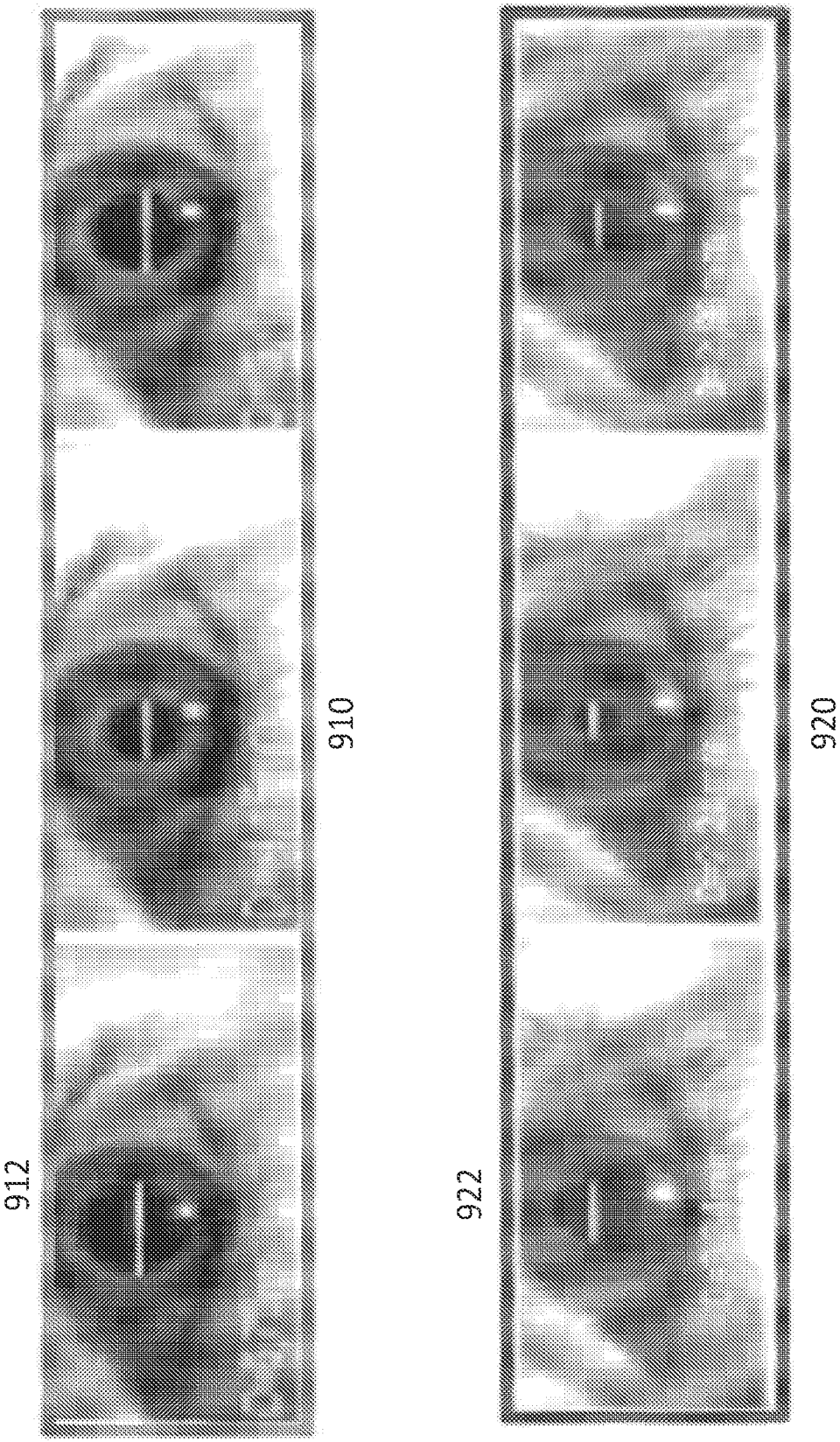
FIG. 9 shows exemplary pupillary constriction, according to an embodiment of the present disclosure.
Figure 10:
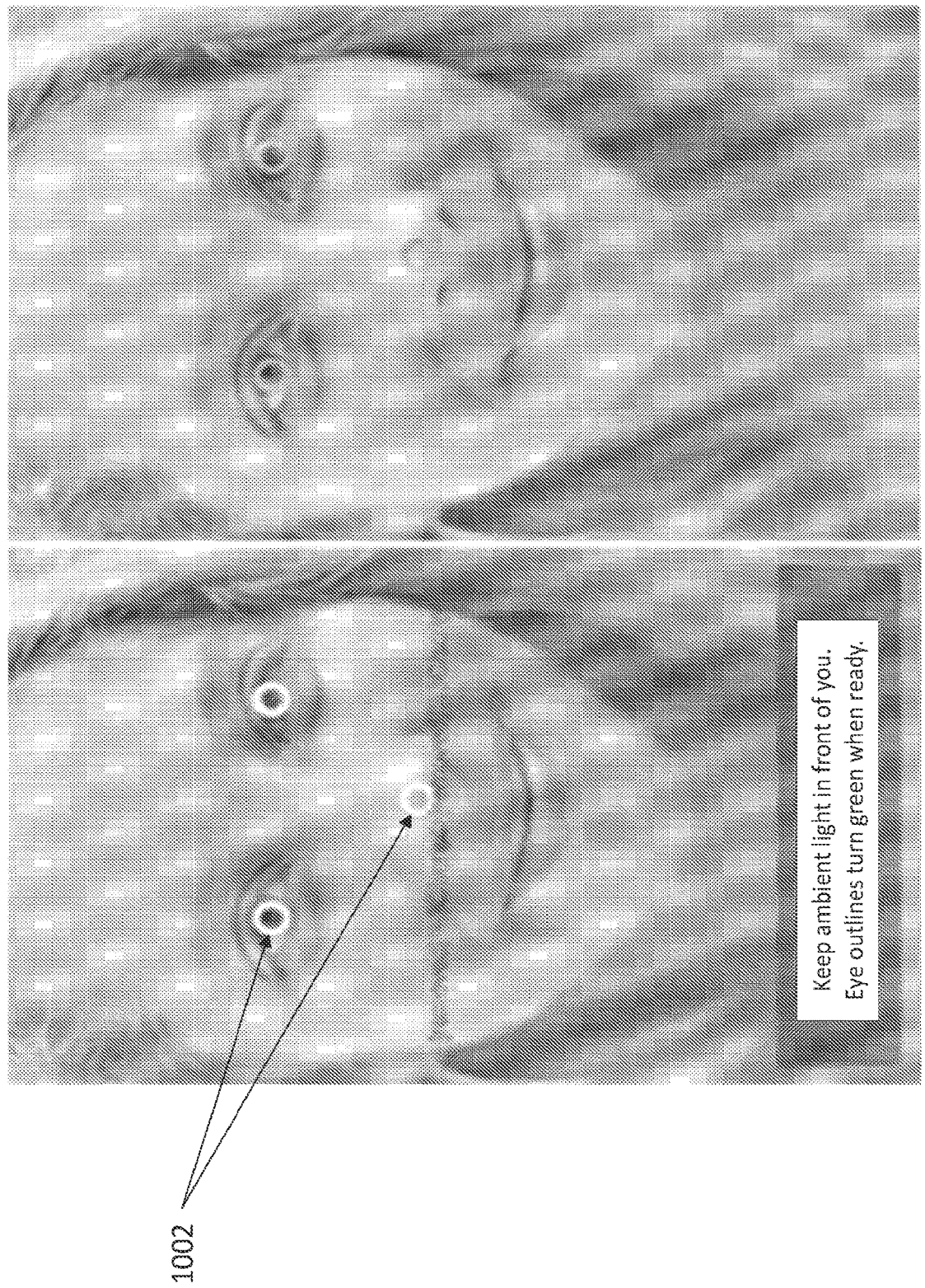
FIG. 10 shows an exemplary software application implementation which automatically detects proper placement, according to an embodiment of the present disclosure.
Figure 11:
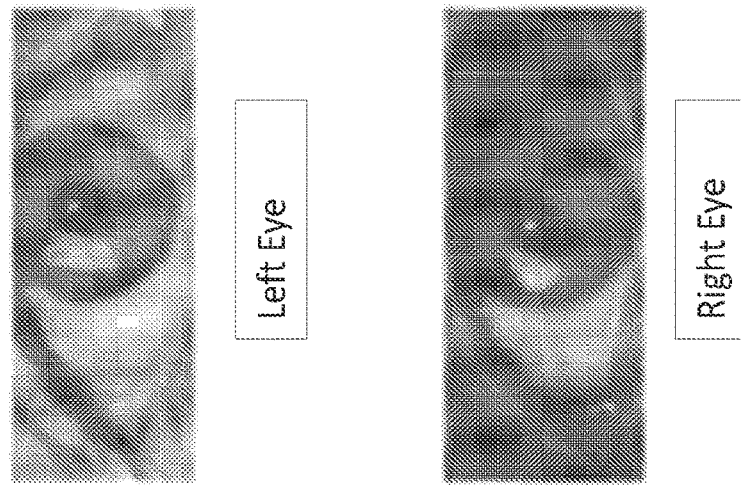
FIG. 11 shows exemplary eye bounding detection, according to an embodiment of the present disclosure.
Figure 11:
Figure 11:
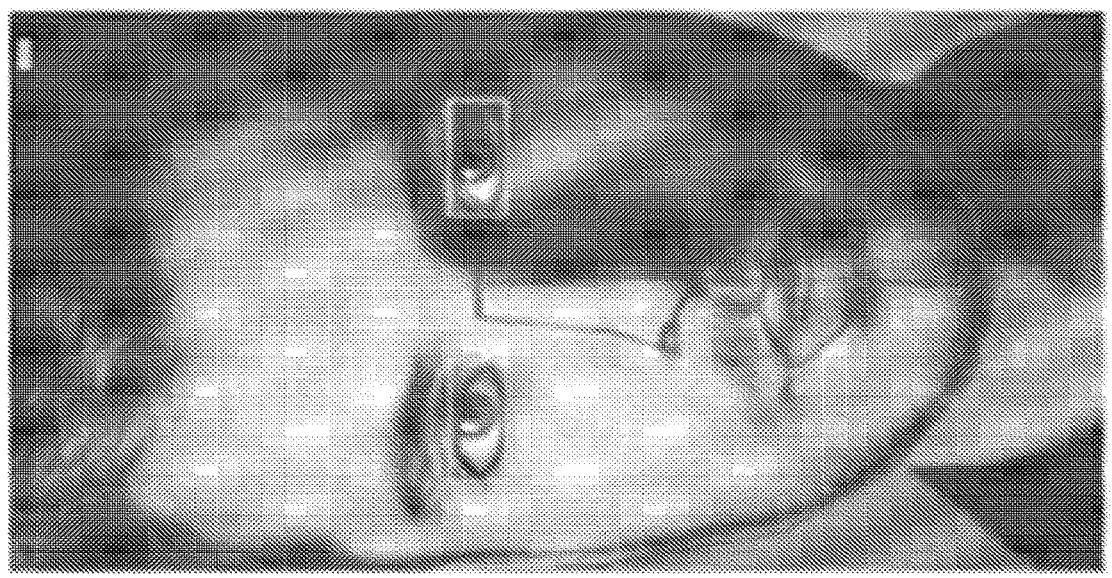

FIG. 9 shows exemplary pupil diameter measurements. For example, 912 and 922 show a baseline pupil diameter for subjects 910 and 920, respectively. Subjects can have different baseline pupil diameters and also different pupillary responses. MCV and MCA can be calculated based on the methods discussed herein.

Identifying Multiple Pupil Responses

Figure 12:
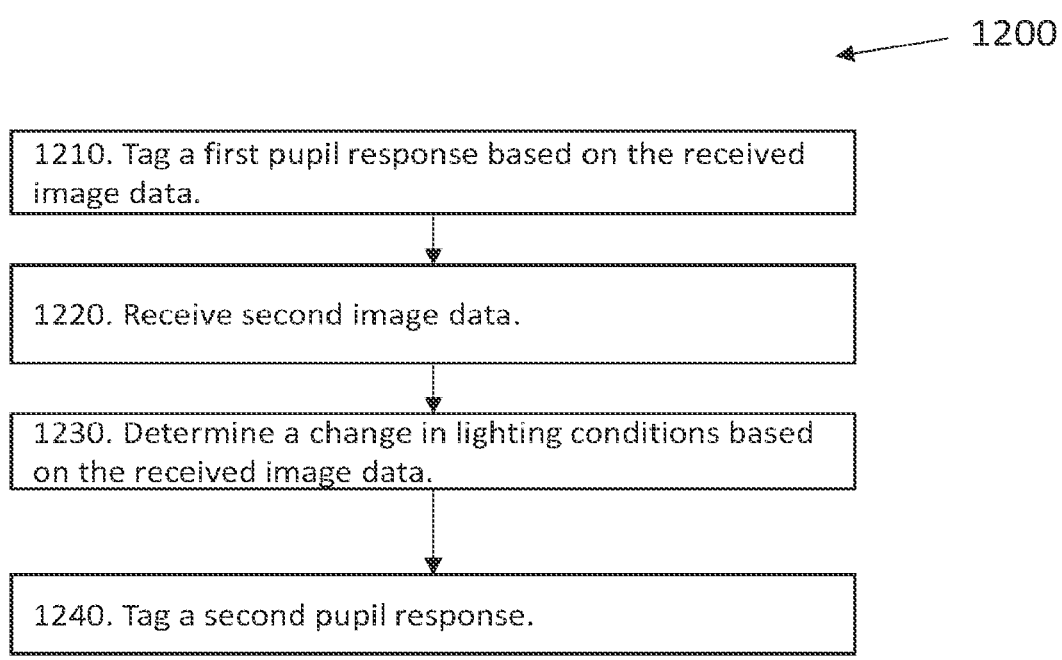
FIG. 12 shows an exemplary methodology for identifying a second pupillary response, according to an embodiment of the present disclosure.

In some examples of the present disclosure, a method is provided to identify multiple pupillary responses. For example, such a method identifies whether an image data set is adulterated by unintentional pupil stimulation (e.g., whether pupillary reflexes in response to changes in ambient light is being measured rather than pupillary psychosensory responses). FIG. 12 shows an exemplary methodology 1200 for identifying and tagging unintentional pupil responses, according to an embodiment of the present disclosure. For example, methodology 1200 can be performed before, during, and/or after methodology 300 of FIG. 3.

Methodology 1200 of FIG. 12 provides for first, at 1210, tagging a first pupil response based on the received image data. For example, the first pupil response includes a change in any of the pupil features as discussed herein.

Methodology 1200 then provides for, at 1220, receiving second image data, after the originally-received image data.

Methodology 1200 then provides for, at 1230, determining a change in lighting conditions. For example, the change in light conditions can be determined based on a brightness difference between the received image data from 1210 and the received second image data from 1220.

Methodology 1200 then provides for tagging a second pupil response in the second image data, at 1240. For example, if the second image data is a series of images, 1240 provides for identifying the image or images which occur simultaneously, or close in time afterwards to the change in lighting conditions. In some examples, the second pupil response is identified as any one of the pupil features discussed herein.

Infrared Measurements Implementation

Figure 13:
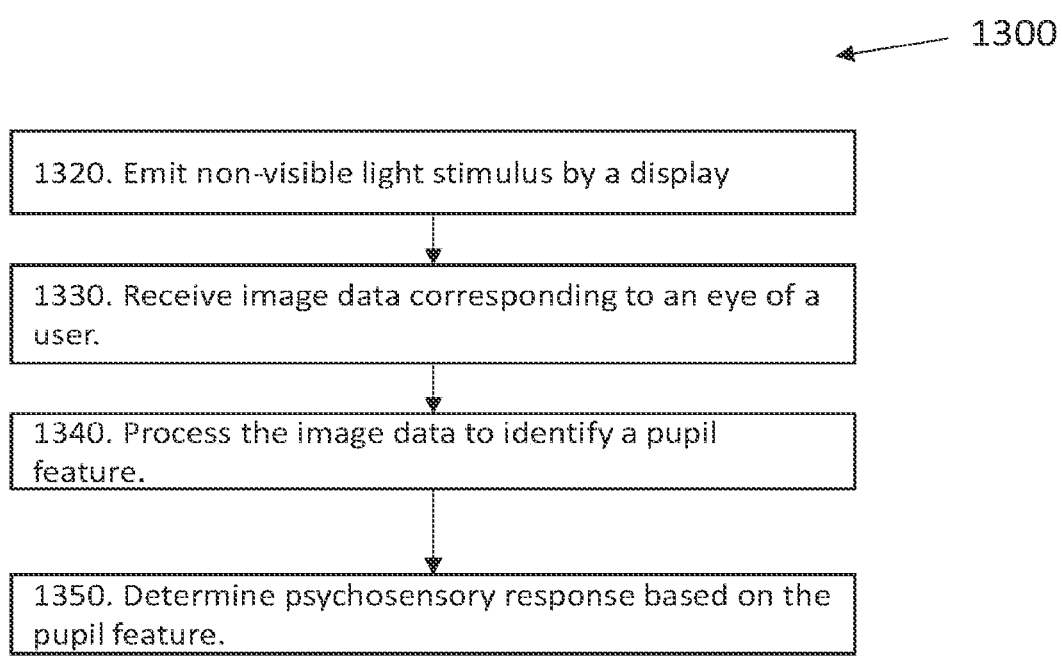
FIG. 13 shows an exemplary methodology for measuring pupillary response with non-visible light, according to an embodiment of the present disclosure.

The present disclosure further provides for image capture with non-visible light and/or an infrared camera. For example, the sensor 116 and/or the display 112 of FIG. 1 can provide a non-visible light stimulus. In some examples, the camera 114 is an infrared camera. FIG. 13 shows an exemplary methodology 1300, which can be performed on systems 100 and/or 200 of FIGS. 1 and 2, respectively.

Methodology 1300 provides for, at 1320, emitting a non-visible light stimulus by a display (e.g., the display 112 or the sensor 116 of FIG. 1). The non-visible light stimulus is configured to illuminate the user's face sufficient to cause a high enough image contrast (sufficiently high enough for pupil-iris segmentation). 1320, therefore, makes use of the high-image contrast that is provided by infrared light generally. For example, the non-visible light stimulus provided at 1320 is a light stimulus with a wavelength between 600 nm and 1000 nm.

Because 1320 provides the illumination sufficient to provide high enough image contrast, methodology 1300 requires less ambient light.

Methodology 1300 further provides for receiving, at 1330, image data corresponding to an eye of a user. In some examples, the image data received is a set of images or a video. In some examples, the set of images are collected at regular intervals (e.g., intervals measured in seconds, milliseconds, and/or microseconds) for a period of time (e.g., over one minute, two minutes, three minutes). In some examples, the image data received at 1330 is received from an infrared camera.

Methodology 1300 further provides, at 1340, for processing the image data to identify a pupil feature and an iris feature. For example, the received image data is processed according to any of the methodologies discussed with respect to 304 and 306 of methodology 300 of FIG. 3. Methodology 1300 then provides for, at 1350, determining psychosensory responses based on the pupil feature, which is analogous to 310 of methodology 300 of FIG. 3. Since pupillary response is dynamic, some implementations of the present disclosure can be used in a first phase of authentication. For example, face identification can begin with checking pupillary response prior to facial recognition. Depth perception and temperature sensing are easier to manipulate when compared to pupillary response.

Therefore, methodology 1300 avoids confounding pupillary response results with additional, unintentional stimulus. Although methodology 1300 is described using measurements from one eye of the user, in some implementations, two eyes of the user are independently measured. Two independent measurements allow a comparison of results from both eyes to possibly confirm measurement results.

The methodology 300 and the methodology 1300 can be repeated at various points in time (e.g., over months, days, or years). Characteristics or metrics of the psychosensory responses obtained over the various points in time can be compared to each other to obtain trends or relationships of the metrics. In retrospective analysis, trends can help inform on disease progression or onset. In prospective analysis, trends can help predict future performance or future diseased states. Points in time as used herein refer to individual sessions. A session can span a period of time, thus, analytical results from different sessions can be compared and contrasted.

Experimental Data

Figure 14:
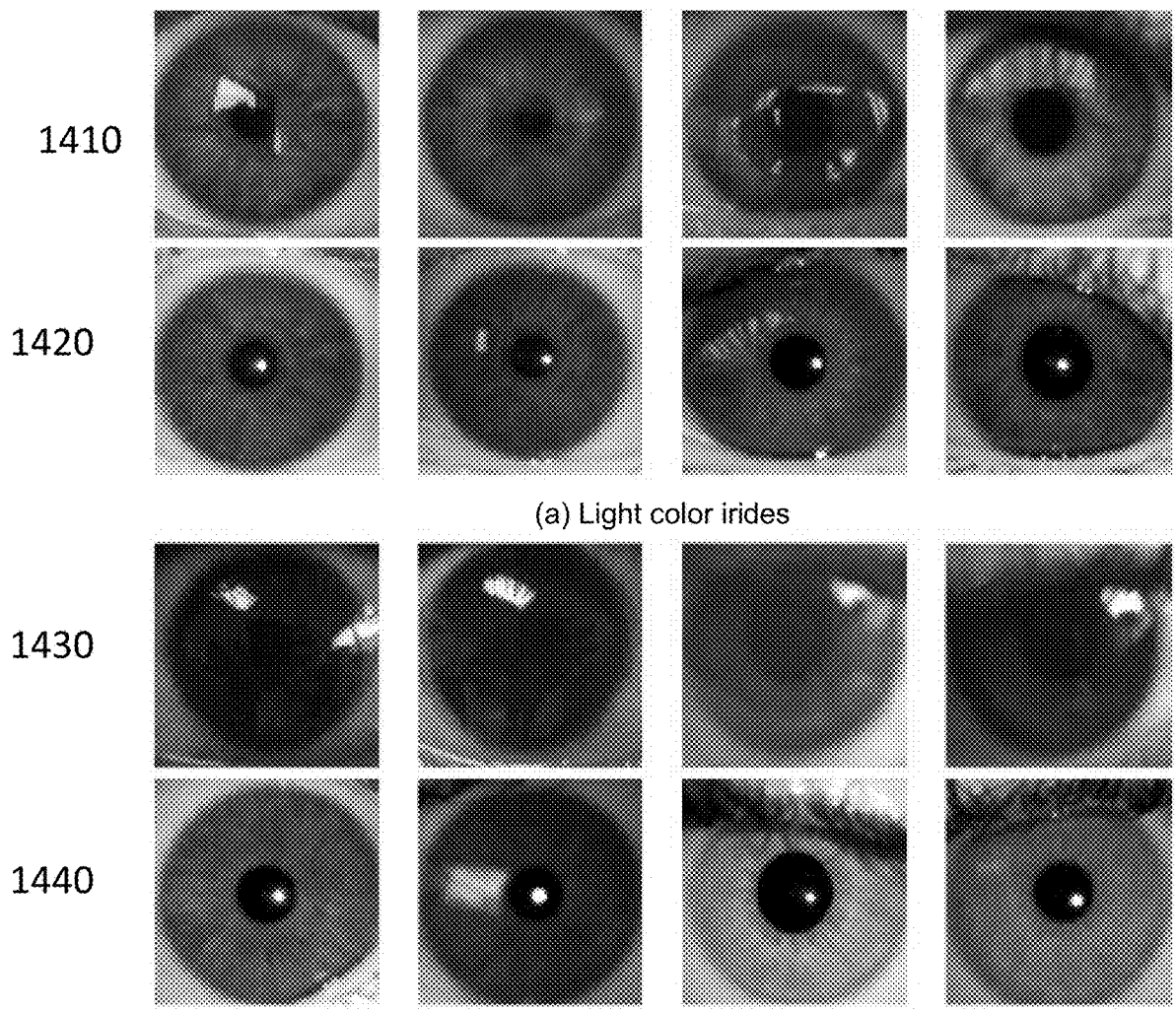
FIG. 14 compares exemplary data for pupil-iris segmentation between visible light and non-visible light, according to an embodiment of the present disclosure.

FIG. 14 shows exemplary image data as compared between sets of images taken in visible light (image sets 1410 and 1430) and sets of images taken in infrared light (image sets 1420 and 1440). Image sets 1420 and 1440 show much clearer delineation between the pupil and the iris of the subject than the image sets 1410 and 1430, which are taken in visible light. In particular, image set 1430 is taken of a dark iris, and pupil segmentation is almost impossible due to the similarity of the colors of the pupil and the iris, and a low contrast between the two. Therefore, FIG. 14 demonstrates the utility of methodology 1300 of FIG. 13, which collects image data with non-visible stimulus.

Embodiments of the present disclosure provide systems and methods for determining pupillary psychosensory response. In some implementations, pupillary psychosensory response can be used as digital biomarkers for drug use and Alzheimer's disease. For example, as shown in FIG. 7, a control group can be used to characterize measurements from other groups with mild cognitive impairments. As such, pupillary psychosensory response has the potential to detect cognition and neurodegeneration. Exact causes of cognitive impairment may be determined using objective markers that provide additional information. For example, drug use and Alzheimer's disease affect the brain through distinct molecular pathways, however, both share a common phenotype (cognitive impairment) when expressed. If cognitive impairment is detected, then additional objective markers can be used to determine whether the cognitive impairment is due to drug use or other factors.

The pupillary psychosensory response pathway corresponds to the pupil dilation pathway, which is innervated by the sympathetic nervous system and controlled by the dilator pupillae. Pupillary psychosensory response has a broad range of applications including identifying deception, cognitive load, stress, interest, and emotion.

Additionally, pupillary responses have been shown to reflect activity in the locus coeruleus, responsible for mediating the sympathetic nervous system, where degeneration has been discovered in the early stages of Alzheimer's disease. Studies show that tau protein misfolding may initially occur in the locus coeruleus and that the formation of pre-tangle pathology first appears in its long projections before spreading to the cortex. Furthermore, abnormal locus coeruleus cell loss becomes more prominent throughout Alzheimer's disease progression. The severity of locus coeruleus degeneration is also correlated with the severity of dementia and cognitive impairment. Therefore, there are known links between pupillary psychosensory response and the functioning of the locus coeruleus system, as well as potential links between locus coeruleus function and Alzheimer's disease. Thus, pupillary psychosensory response may serve as a digital biomarker to brain system function that is affected in the earliest phases of Alzheimer's disease. Pupillary response can be used as a proxy for locus coeruleus dysfunction and can be used as a digital biomarker of early MCI and Alzheimer's disease risk before noticeable cognitive decline.

Figure 15:
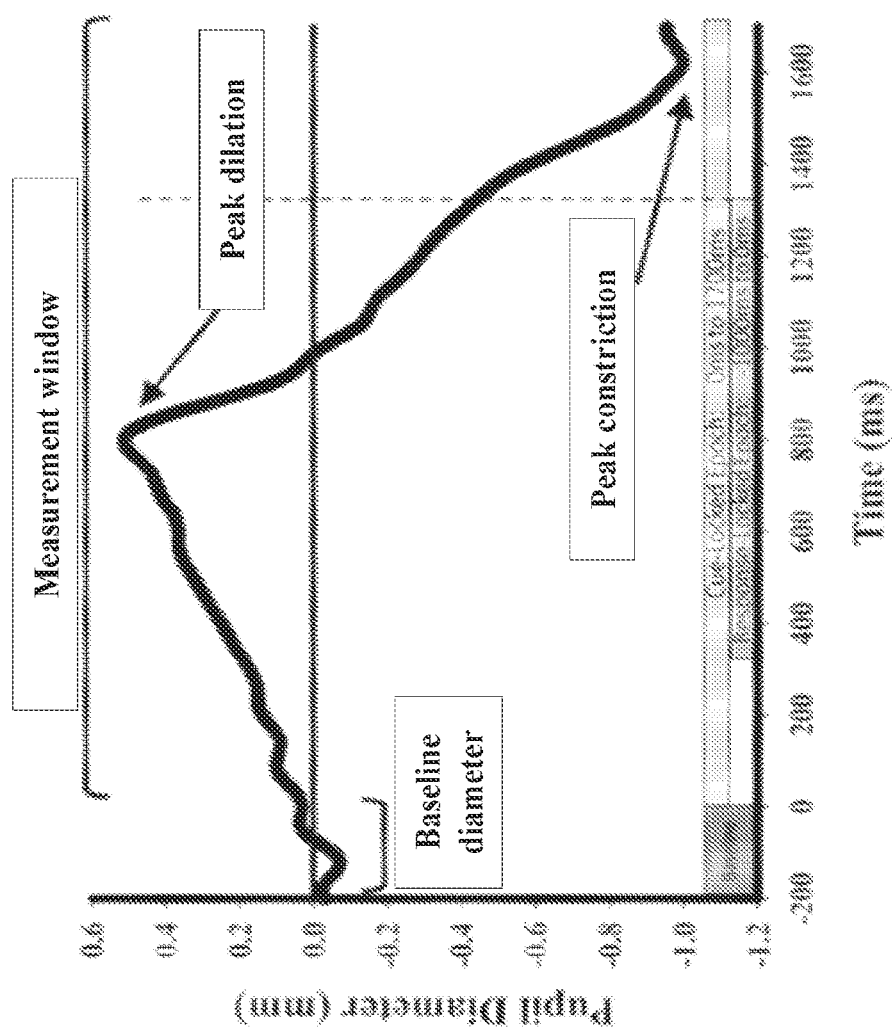
FIG. 15 illustrates an example psychosensory pupil response curve with metrics that can be determined in a measurement window, according to an embodiment of the present disclosure.

FIG. 15 illustrates an example psychosensory pupil response curve with different metrics that can be determined in a measurement window. Given a baseline diameter of the pupil of a subject, the diameter can change over time by dilating or constricting. FIG. 15 shows a peak dilation and a peak constriction. The psychosensory pupil response of FIG. 15 can provide different metrics that can be observed, including, peak dilation, peak constriction, peak-to-peak difference (which measures difference between peak dilation and peak constriction), and area under the psychosensory pupil response curve.

Increased cognitive load is significantly associated with increased dilation, increased peak-to-peak difference, and reduced peak constriction. Individuals with MCI show significantly reduced peak dilation in response to cognitive load. Reduced dilation in response to cognitive load may be associated with locus coeruleus degeneration, a known indicator for Alzheimer's disease. Depressed adults have demonstrated increased pupil dilation in response to negative emotional stimuli. Reduced pupil dilation to emotional expression has been linked to increased risk for depression, following a stressful experience. Increased stress is associated with increased pupil dilation. Individuals who are fatigued have reduced pupil dilation.

Figure 16:
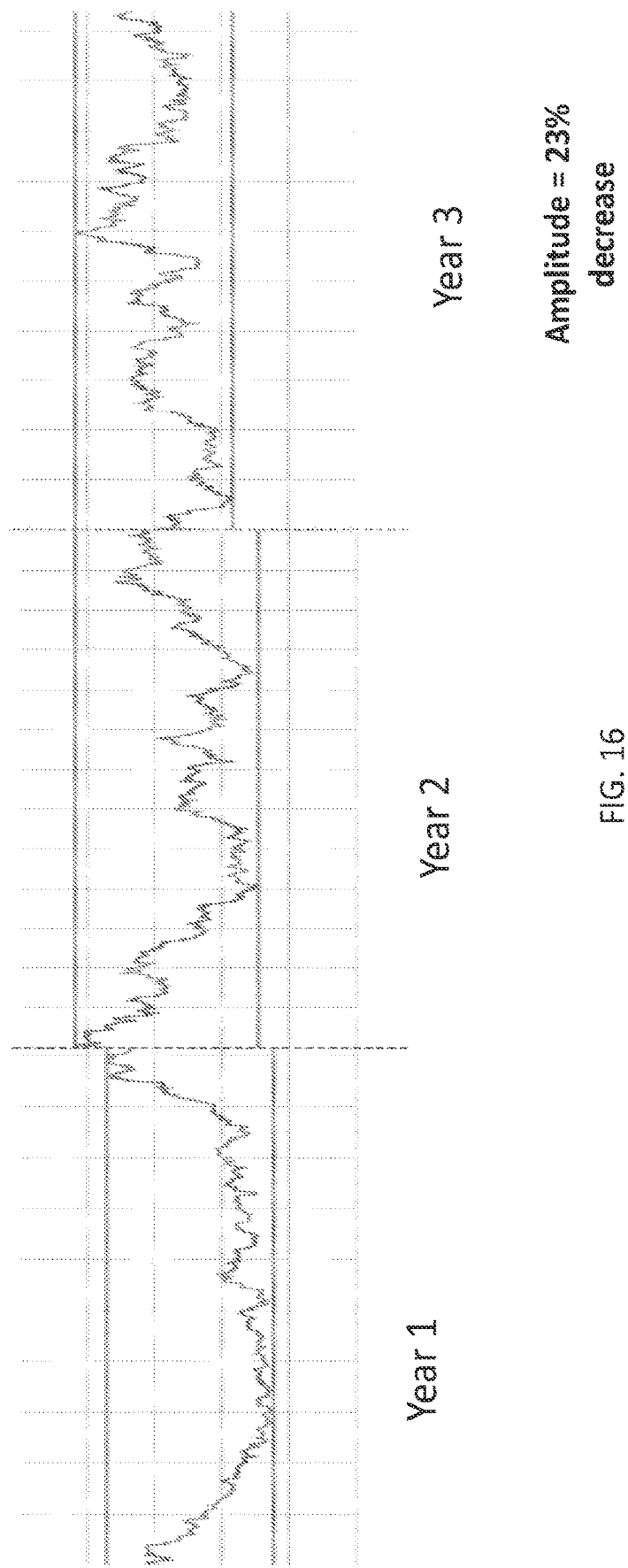
FIG. 16 shows a psychosensory pupil response graph over time for three different time periods for an individual, according to an embodiment of the present disclosure.

FIG. 16 shows psychosensory pupil response graph over time for three different time periods for a same individual, according to some implementations of the present disclosure. Amplitudes for year 1 and year 2 are comparable, and amplitude for year 3 is lower than amplitudes for year 1 and year 2. The amplitude decrease from year 1 to year 3 is about 23 percent decrease. Using some embodiments of the present disclosure, psychosensory pupil response can be captured for the same individual over time to monitor cognitive decline. Decreased maximum peak-to-peak dilation over time of the psychosensory pupil response can be associated with MCI as discussed above.

Figure 17:
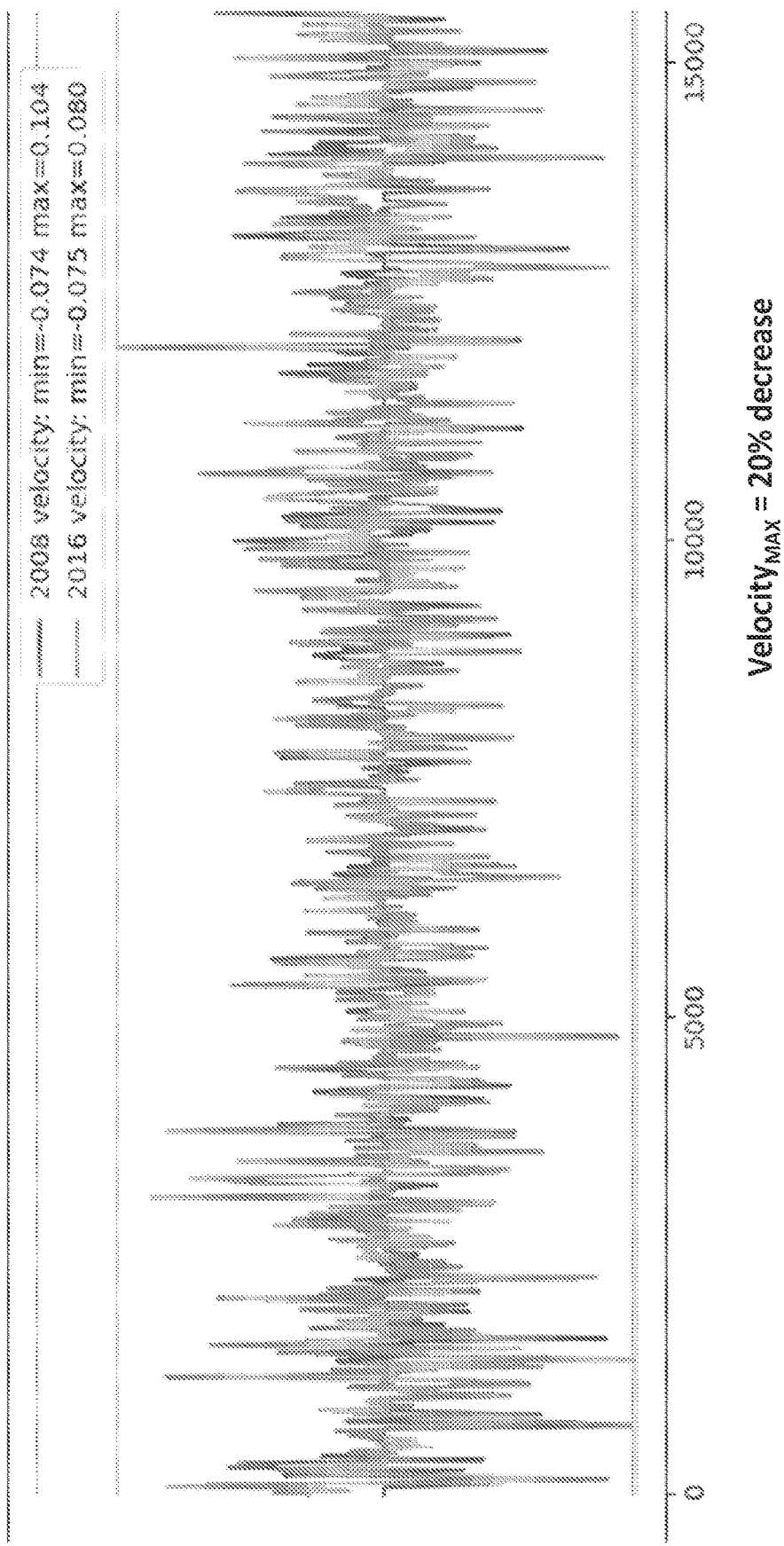
FIG. 17 shows an overlay of two psychosensory pupil response graphs at two different time periods for an individual, according to an embodiment of the present disclosure.

FIG. 17 shows an overlay of two psychosensory pupil response graphs at two different time periods for a same individual, according to some implementations of the present disclosure. How quickly the pupil dilates or constricts can be measured as a velocity parameter. Decrease in maximum velocity from 0.104 in 2008 to 0.08 in 2016 is an indication of cognitive decline over time.

Embodiments of the present disclosure allow using pyschosensory pupil response to perform a retrospective longitudinal analysis to determine cognitive ability of an individual. Previously recorded videos of the individual at different time periods (e.g., different years as provided in FIGS. 16 and 17) can be processed and analyzed. In a telemedicine example, the individual can be suspected of having developed dementia so the individual captures videos of herself. The captured video can be compared to previous videos of the individual over a period of 5 to 10 years. The individual may have captured 5 videos of herself over the 5 to 10 year timeframe. The different videos are analyzed to extract various metrics that are consistent with developing dementia (e.g. decreasing peak-to-peak amplitude over time as shown in FIG. 16).

In some implementations, prospective longitudinal analysis can be performed using psychosensory pupil response to predict cognitive ability of an individual in the future. Using previously obtained video data at different points in time (e.g., over a 5 to 10-year span), various metrics (e.g., peak-to-peak amplitude, maximum velocity, etc.) can be determined for the different points in time. A trend for the various metrics can be determined, and the trend can be used to predict future cognitive ability of the individual.

In some implementations, analysis of psychosensory pupil response is performed for only one point in time. For example, a stimulus can be presented to an individual in the form of a mathematical problem. The stimulus can be provided to the individual visually via a screen (e.g., the display 112 of the system 100) or aurally (e.g., a speaker of the system 100). Video of the individual's pupils can be captured (e.g., using the camera 114 of the system 100) while the individual is solving the mathematical problem.

In other examples, the stimulus could be a variety of audio, visual, text based stimulus that might be presented through a mobile or other device. For instance, the stimulus could be an image shown to a user (e.g. a baby) and the system may determine a cognitive response based on the image. In some examples, the stimulus may be an audio stimulus or question. Accordingly, the system may assist in communication with a baby, or other user.

In some implementations, analysis of the psychosensory pupil response may be performed to determine whether a change in response occurs within temporal proximity of a presentation of a stimulus on a device. In one example, the system may display a stimulus, record a time stamp of the display stimulus, and compare the temporal proximity of any change in the pupil response in relation to the stimulus. For instance, the system may determine whether a response occurred within an expected time window following presentation of the stimulus, based on the time stamp of the captured frames that show the psychosensory pupil response.

Accordingly, responses that occur in frames with a time stamp outside the expected time window following presentation of the stimulus (e.g. time stamp of displaying a math problem or an auditory stimulus) may be filtered.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. An electronic device for evaluating pupillary psychosensory response, the electronic device comprising a processor and a non-transitory computer readable medium with computer-executable instructions stored thereon, such that when the instructions are executed the electronic device is configured to:
   receive video data for multiple sessions, the video data for each of the multiple sessions comprising at least two frames;
   locate, for each of the multiple sessions, one or more eye objects in a first frame of the at least two frames;
   extract, for each of the multiple sessions, within the first frame, a corresponding iris object for each of the one or more eye objects;
   extract, for each of the multiple sessions, within the first frame, a corresponding pupil object for each of the one or more eye objects;
   compute, for each of the multiple sessions, a first set of indexes for the one or more eye objects located in the first frame, the first set of indexes being a first set of pupil-to-iris ratios;
   compute, for each of the multiple sessions, subsequent sets of pupil-to-iris ratios for subsequent frames of the at least two frames, each of the subsequent sets of pupil-to-iris ratios pertaining to the one or more eye objects located in the first frame and also in each of the subsequent frames; and
   determine, for each of the multiple sessions, the pupillary psychosensory response based at least in part on the first set of pupil-to-iris ratios and the subsequent sets of pupil-to-iris ratios;
   determine a trend based at least in part on the pupillary psychosensory responses for the multiple sessions; and
   determine that the trend indicates cognitive decline over the multiple sessions based at least in part on a reduction of amplitude of peak-to-peak difference over the multiple sessions.

2. The electronic device of claim 1, further configured to locate the one or more eye objects in the first frame using one or more image processing techniques including machine learning, Haar cascades, or deep learning.

3. The electronic device of claim 1, wherein the video data is previously recorded and the pupillary psychosensory response is determined retrospectively.

4. The electronic device of claim 1, wherein the pupillary psychosensory response is determined based on one of a pupil dilation and a pupil constriction.

5. The electronic device of claim 1, wherein the first set of pupil-to-iris ratios is computed based at least in part on a diameter of the corresponding pupil object and a diameter of the corresponding iris object.

6. The electronic device of claim 1, further configured to:
   compute a first set of iris surface areas for each iris object in the one or more eye objects located in the first frame; and compute a first set of pupil surface areas for each pupil object in the one or more eye objects located in the first frame, wherein the first set of pupil-to-iris ratios for the one or more eye objects is computed based on the first set of iris surface areas and the first set of pupil surface areas.

7. The electronic device of claim 1, further configured to: compute a first set of pupil diameters for each pupil object in the one or more eye objects located in the first frame based on a distance from a camera that captured the first frame.

8. The electronic device of claim 1, wherein the one or more eye objects are two or more eye objects belonging to at least two individuals.

9. The electronic device of claim 1, wherein the first set of pupil-to-iris ratios and the subsequent sets of pupil-to-iris ratios indicate a pupil-to-iris ratio trend for a first eye object in the one or more eye objects, and wherein determining the pupillary psychosensory response includes determining from the pupil-to-iris ratio trend for the first eye object denoting that an individual to which the first eye object belongs experienced at least one of a cognitive effort, stress, sleepiness, interest, drug use, dementia, depression, anxiety, behavior disorder, or any combination thereof.

10. The electronic device of claim 9, wherein the pupil-to-iris ratio trend indicating an increase in the corresponding pupil-to-iris ratio during at least a portion of the first frame and the subsequent frames portrays a psychosensory response of the individual.

11. The electronic device of claim 9, further configured to:
receive one or more objective markers pertaining to the individual; and
determine the pupillary psychosensory response further based at least in part on the one or more objective markers.

12. The electronic device of claim 1, wherein the determine the pupillary psychosensory response includes determining metrics associated with the pupillary psychosensory response, the metrics including one or more of: peak dilation, peak constriction, velocity of dilation, or peak-to-peak difference.

13. A method for evaluating pupillary psychosensory response, comprising:
receiving video data for multiple sessions, the video data for each of the multiple sessions including at least two frames;
locating, for each of the multiple sessions, one or more eye objects in a first frame of the at least two frames;
extracting, for each of the multiple sessions, within the first frame, a corresponding iris object for each of the one or more eye objects;
extracting, for each of the multiple sessions, within the first frame, a corresponding pupil object for each of the one or more eye objects;
computing, for each of the multiple sessions, a first set of pupil-to-iris ratios for the one or more eye objects located in the first frame; and
computing, for each of the multiple sessions, subsequent sets of pupil-to-iris ratios for subsequent frames of the at least two frames, each of the subsequent sets of pupil-to-iris ratios pertaining to the one or more eye objects located in the first frame and also in each of the subsequent frames; and
determining, for each of the multiple sessions, the pupillary psychosensory response based at least in part on the first set of pupil-to-iris ratios and the subsequent sets of pupil-to-iris ratios;
determining a trend based at least in part on the pupillary psychosensory responses for the multiple sessions; and
determining that the trend indicates cognitive decline over the multiple sessions based at least in part on a reduction of amplitude of peak-to-peak difference over the multiple sessions.

14. A method for evaluating pupillary psychosensory response for multiple sessions, comprising:
receiving video data for the multiple sessions, the video data for each of the multiple sessions including at least two frames;
computing, for each of the multiple sessions, a first set of pupil-to-iris ratios for one or more eye objects located in a first frame of the at least two frames; and
computing, for each of the multiple sessions, subsequent sets of pupil-to-iris ratios for subsequent frames of the at least two frames, each of the subsequent sets of pupil-to-iris ratios pertaining to the one or more eye objects located in the first frame and also in each of the subsequent frames; and
determining, for each of the multiple sessions, the pupillary psychosensory response based at least in part on the first set of pupil-to-iris ratios and the subsequent sets of pupil-to-iris ratios;
determining a trend based at least in part on the pupillary psychosensory responses for the multiple sessions; and
determining that the trend indicates cognitive decline over the multiple sessions based at least in part on a reduction of amplitude of peak-to-peak difference over the multiple sessions.

15. The method of claim 14, further comprising:
determining that the trend indicates cognitive decline for a future session not included in the multiple sessions, based at least in part on a reduction of amplitude of peak-to-peak difference over the multiple sessions.

16. The method of claim 14, wherein the multiple sessions span a time period of greater than one year, and the trend is indicative of cognitive performance over the time period.

17. The method of claim 14, further comprising:
determining a predicted date in the future when the trend will cross a predefined threshold that will indicate a change in mental health status.

18. The method of claim 14, wherein the pupillary psychosensory response for at least one of the multiple sessions comprises one of a change in dilation amplitude and a change in constriction amplitude over a baseline established within an initial 5, 10, 15, 20, 25, 30, 35, 40, 45 or greater seconds of video.

* * * * *